(12) United States Patent
Bischof et al.

(10) Patent No.: US 11,072,569 B2
(45) Date of Patent: *Jul. 27, 2021

(54) NORMAL ALPHA OLEFIN SYNTHESIS USING DEHYDROFORMYLATION OR DEHYDROXYMETHYLATION

(71) Applicant: Chevron Phillips Chemical Company LP, The Woodlands, TX (US)

(72) Inventors: Steven M. Bischof, Humble, TX (US); Vy M. Dong, Irvine, CA (US); Faben A. Cruz, Irvine, CA (US); Xuesong Wu, Irvine, CA (US); Stephen Karl Murphy, Cambridge, MA (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/920,835

(22) Filed: Jul. 6, 2020

(65) Prior Publication Data

US 2020/0331823 A1 Oct. 22, 2020

Related U.S. Application Data

(63) Continuation of application No. 16/283,892, filed on Feb. 25, 2019, now Pat. No. 10,723,672.

(60) Provisional application No. 62/634,979, filed on Feb. 26, 2018.

(51) Int. Cl.
| | | |
|---|---|---|
| *C01C 1/20* | (2006.01) |
| *C07C 1/20* | (2006.01) |
| *B01J 31/22* | (2006.01) |
| *B01J 31/02* | (2006.01) |
| *C07C 1/207* | (2006.01) |
| *C07C 67/297* | (2006.01) |
| *C07C 6/04* | (2006.01) |
| *C07C 29/48* | (2006.01) |
| *C07C 41/18* | (2006.01) |
| *C07C 29/03* | (2006.01) |
| *C07J 9/00* | (2006.01) |
| *C07C 45/50* | (2006.01) |

(52) U.S. Cl.
CPC ............ *C07C 1/20* (2013.01); *B01J 31/0204* (2013.01); *B01J 31/0271* (2013.01); *B01J 31/2295* (2013.01); *C07C 1/2076* (2013.01); *C07C 6/04* (2013.01); *C07C 29/03* (2013.01); *C07C 29/48* (2013.01); *C07C 41/18* (2013.01); *C07C 45/50* (2013.01); *C07C 67/297* (2013.01); *C07J 9/00* (2013.01); *B01J 2231/70* (2013.01); *B01J 2531/822* (2013.01); *C07C 2531/02* (2013.01); *C07C 2531/22* (2013.01); *C07C 2531/24* (2013.01); *C07C 2601/20* (2017.05)

(58) Field of Classification Search
CPC ......... C07C 1/2076; C07C 11/02; C07C 1/20; C07C 29/03; C07C 29/48; C07C 41/18; C07C 45/50; C07C 67/297; C07C 6/04; C07C 11/12; C07C 13/275; C07C 15/44; C07C 15/46; C07C 31/125; C07C 31/20; C07C 43/215; C07C 47/02; C07C 69/78; C07C 2531/02; B01J 2231/70; B01J 2531/822; B01J 31/0204; B01J 31/0271; B01J 31/2295

See application file for complete search history.

(56) References Cited

U.S. PATENT DOCUMENTS 10,183,899 B2 * 1/2019 Bischof .................. C07C 45/50
10,723,672 B2 * 7/2020 Bischof ................ B01J 31/0204

* cited by examiner

*Primary Examiner* — Sharon Pregler
(74) *Attorney, Agent, or Firm* — Merchant & Gould, P.C.

(57) ABSTRACT

The present invention discloses processes for producing normal alpha olefins, such as 1-hexene, 1-octene, 1-decene, and 1-dodecene in a multistep synthesis scheme from another normal alpha olefin. Also disclosed are reactions for converting aldehydes, primary alcohols, and terminal vicinal diols into normal alpha olefins.

19 Claims, No Drawings

US 11,072,569 B2

NORMAL ALPHA OLEFIN SYNTHESIS USING DEHYDROFORMYLATION OR DEHYDROXYMETHYLATION

REFERENCE TO RELATED APPLICATION

This application is a continuation application of U.S. patent application Ser. No. 16/283,892, filed on Feb. 25, 2019, now U.S. Patent No. 10,723,672, which claims the benefit of U.S. Provisional Patent Application No. 62/634,979, filed on Feb. 26, 2018, the disclosures of which are incorporated herein by reference in their entirety.

FIELD OF THE INVENTION

The present disclosure relates generally to methods for making normal alpha olefins from aldehydes, primary alcohols, and terminal vicinal diols.

BACKGROUND OF THE INVENTION

The synthesis of specific carbon number normal alpha olefins, whether directly from another compound having an alcohol or aldehyde functional group, or via a multistep synthesis scheme from another normal alpha olefin, is of significant importance in the chemical industry. It would be beneficial to develop such reactions and synthesis schemes to produce desirable normal alpha olefin products. Accordingly, it is to these ends that the present invention is generally directed.

SUMMARY OF THE INVENTION

This summary is provided to introduce a selection of concepts in a simplified form that are further described herein. This summary is not intended to identify required or essential features of the claimed subject matter. Nor is this summary intended to be used to limit the scope of the claimed subject matter.

Catalyst compositions that can be used in oxidative dehydroxymethylation and oxidative dehydroformylation processes to produce normal alpha olefins are disclosed herein. Such catalyst compositions can comprise a transition metal compound, a phosphine, and a heteroatomic acid or heteroatomic acid derivative, or a phosphine transition metal compound complex and a heteroatomic acid or heteroatomic acid derivative. These catalyst compositions can further comprise an acceptor, which is typically an olefinic compound.

A dehydroxymethylation process consistent with aspects of this invention can comprise contacting a saturated linear $C_3$-$C_{36}$ hydrocarbon primary alcohol with the catalyst composition to form a $C_2$-$C_{35}$ normal alpha olefin. Another dehydroxymethylation process consistent with aspects of this invention can comprise contacting a saturated linear $C_4$-$C_{36}$ hydrocarbon terminal vicinal diol with the catalyst composition to form a $C_2$-$C_{34}$ normal alpha olefin. In yet another aspect, a dehydroformylation process is disclosed, and the dehydroformylation process can comprise contacting a saturated linear $C_3$-$C_{36}$ hydrocarbon aldehyde with the catalyst composition to form a $C_2$-$C_{35}$ normal alpha olefin.

Processes for producing normal alpha olefins using multistep synthesis schemes also are disclosed and described herein. One such process can comprise (i) conducting a hydroboration-oxidation reaction of a first normal alpha olefin having the structure $CH_3(CH_2)_n HC=CH_2$ to form a linear primary alcohol having the structure $CH_3(CH_2)_{n+1} CH_2OH$, and (ii) contacting the linear primary alcohol with a dehydroxymethylation catalyst composition to form a second normal alpha olefin having the structure $CH_3(CH_2)_{n-1} HC=CH_2$. Another process can comprise (i) conducting a dihydroxylation reaction of a first normal alpha olefin having the structure $CH_3(CH_2)_n HC=CH_2$ to form a terminal vicinal diol having the structure $CH_3(CH_2)_n CH(OH)CH_2OH$, and (ii) contacting the terminal vicinal diol with a dehydroxymethylation catalyst composition to form a second normal alpha olefin having the structure $CH_3(CH_2)_{n-2} HC=CH_2$. In these processes, n is an integer that can range from 2 to 33.

Another process for producing a normal alpha olefin using a multistep synthesis scheme can comprise (i) contacting a first normal alpha olefin having the structure $CH_3(CH_2)_n HC=CH_2$ and a metathesis catalyst system to form a linear internal olefin having the structure $CH_3(CH_2)_n HC=CH(CH_2)_n CH_3$, (ii) contacting the linear internal olefin with a hydroformylation catalyst system, carbon monoxide, and hydrogen to form a linear aldehyde having the formula $CH_3(CH_2)_{2n+3} C(=O)H$, and (iii) contacting the linear aldehyde with a dehydroformylation catalyst composition to form a second normal alpha olefin having the structure $CH_3(CH_2)_{2n+1} HC=CH_2$. In this process, n is an integer that can range from 0 to 15.

Another process for producing normal alpha olefins consistent with aspects of this invention can comprise (a) contacting a linear internal olefin having the structure $CH_3(CH_2)_p HC=CH(CH_2)_q CH_3$ with a hydroformylation catalyst system, carbon monoxide, and hydrogen to form a linear aldehyde having the formula $CH_3(CH_2)_{p+q+3} C(=O)H$, and (b) contacting the linear aldehyde with a dehydroformylation catalyst composition to form a normal alpha olefin having the structure $CH_3(CH_2)_{p+q+1} HC=CH_2$. In this process, p and q can be integers that independently range from 0 to 15.

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects can be directed to various feature combinations and sub-combinations described in the detailed description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects, a combination of different features can be envisioned. For each and every aspect and/or feature disclosed herein, all combinations that do not detrimentally affect the designs, compositions, processes, and/or methods described herein are contemplated with or without explicit description of the particular combination.

Additionally, unless explicitly recited otherwise, any aspect and/or feature disclosed herein can be combined to describe inventive features consistent with the present disclosure.

While compositions and processes/methods are described herein in terms of "comprising" various components or steps, the compositions and processes/methods can also "consist essentially of" or "consist of" the various components or steps, unless stated otherwise. For example, a catalyst composition consistent with aspects of the present invention can comprise; alternatively, can consist essentially of; or alternatively, can consist of; a transition metal compound, a phosphine, and a heteroatomic acid or heteroatomic acid derivative.

The terms "a," "an," and "the" are intended to include plural alternatives, e.g., at least one, unless otherwise specified. For instance, the disclosure of "a normal alpha olefin" or "an acceptor" is meant to encompass one, or combinations of more than one, normal alpha olefin or acceptor, respectively, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; a general reference to a butyl group includes an n-butyl group, a sec-butyl group, an iso-butyl group, and a t-butyl group; and a general reference to cyclododecatriene includes all isomeric forms (e.g., trans,trans,cis-1,5,9-cyclododecatriene, and trans,trans,trans-1,5,9-cyclododecatriene, among other dodecatrienes).

The terms "contact product," "contacting," and the like, are used herein to describe compositions and methods wherein the components are contacted or combined together in any order, in any manner, and for any length of time, unless otherwise specified. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, the term "contacting" is used herein to refer to materials which can be blended, mixed, slurried, dissolved, reacted, treated, or otherwise combined in some other manner. Hence, "contacting" two or more components can result in a mixture, a reaction product, a reaction mixture, etc.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the transition metal compound, the phosphine, the heteroatomic acid or heteroatomic acid derivative, and the acceptor, after combining these components. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, can be used interchangeably throughout this disclosure.

The term "hydrocarbon" whenever used in this specification and claims refers to a compound containing only carbon and hydrogen. The term "olefin" as used herein refers to a hydrocarbon that has at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system, unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s). The term "alpha olefin" as used herein refers to any olefin that has a double bond between the first and second carbon atom of a contiguous chain of carbon atoms. The term "alpha olefin" includes linear and branched alpha olefins and alpha olefins which can have more than one non-aromatic carbon-carbon double bond, unless expressly stated otherwise.

The term "normal alpha olefin" as used herein refers to a linear aliphatic hydrocarbon mono-olefin having a double bond between the first and second carbon atom. The term "linear internal olefin" as used herein refers to a linear aliphatic hydrocarbon mono-olefin having a double bond that is not between the first and second carbon atom, can be further described by the chemical formulas provided throughout this disclosure.

An "aromatic compound" refers to a compound containing a cyclically conjugated moiety that follows the Hückel (4n+2) rule and containing (4n+2) pi-electrons, where n is an integer from 1 to about 5. Aromatic compounds can be monocyclic or polycyclic, unless otherwise specified. Non-limiting examples of aromatic compounds include benzene, naphthalene, and toluene, among others.

As utilized herein, the term "solvent" applies to a material which can dissolve a compound, or a material which can dilute the components of a reaction. As such, the term "solvent" can encompass materials which can act as a diluent, unless stated otherwise.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical moiety having a certain number of carbon atoms is disclosed or claimed, the intent is to disclose or claim individually every possible number that such a range could encompass, consistent with the disclosure herein. For example, the disclosure that a moiety is a $C_1$ to $C_{18}$ hydrocarbyl group, or in alternative language, a hydrocarbyl group having from 1 to 18 carbon atoms, as used herein, refers to a moiety that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ hydrocarbyl group), and also including any combination of ranges between these two numbers (for example, a $C_2$ to $C_4$ and a $C_{12}$ to $C_{16}$ hydrocarbyl group).

The term "about" means that amounts, sizes, formulations, parameters, and other quantities and characteristics are not and need not be exact, but can be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

The present invention is directed generally to catalyst compositions, processes for using the catalyst compositions in oxidative dehydroxymethylation and oxidative dehydroformylation reactions to produce normal alpha olefins, and multistep synthesis schemes to convert a normal alpha olefin into a different normal alpha olefin (i.e., with a different number of carbon atoms).

Beneficially, the disclosed processes can selectively produce normal alpha olefins, while minimizing byproduct alkanes and internal olefins. Also beneficially, the disclosed processes can convert odd carbon number alcohols or aldehydes to even carbon number olefins, and even carbon number diols to even carbon number olefins.

Catalyst Compositions

While not limited thereto, the catalyst compositions disclosed herein can be used in oxidative dehydroxymethylation processes to convert alcohol compounds to normal alpha olefins, and oxidative dehydroformylation processes to convert aldehyde compounds to normal alpha olefins. The catalyst composition can utilize a pre-formed or pre-synthesized transition metal complex, or one in which the components are added together to generate the complex and catalyst in-situ. Thus, for example, the catalyst composition can comprise any suitable transition metal compound, any suitable phosphine, and any suitable heteroatomic acid or heteroatomic acid derivative. Generally, the transition metal compound, the phosphine, and the heteroatomic acid or heteroatomic acid derivative are independent elements of the catalyst composition and are independently described herein. Consequently, the catalyst composition can be described utilizing any combination of the transition metal compound disclosed herein, the phosphine disclosed herein, and the heteroatomic acid or heteroatomic acid derivative disclosed herein. In another aspect, the catalyst composition can comprise any suitable phosphine transition metal compound complex and any suitable heteroatomic acid or heteroatomic acid derivative. In this catalyst composition aspect, the phosphine transition metal compound complex and the heteroatomic acid or heteroatomic acid derivative are independent elements of the catalyst composition and are independently described herein. Consequently, the catalyst composition can be described utilizing any combination of the phosphine transition metal compound complex disclosed herein and the heteroatomic acid or heteroatomic acid derivative disclosed herein.

The transition metal of the transition metal compound or the phosphine transition metal compound complex can be a Group 3 to Group 10 transition metal, a Group 4 to Group 11 transition metal, a Group 4 to Group 9 transition metal, a Group 8 to Group 10 transition metal, or a Group 9 transition metal. For instance, the transition metal of the transition metal compound or the phosphine transition metal compound complex can be cobalt, rhodium, or iridium; alternatively, cobalt; alternatively, rhodium; or alternatively, iridium. Accordingly, in an aspect of this invention, the transition metal compound or the transition metal compound of the phosphine transition metal compound complex can comprise a rhodium compound, non-limiting examples of which can include an olefin rhodium alkoxide complex, a cyclodiene rhodium alkoxide complex, or any combination thereof alternatively, an olefin rhodium alkoxide complex; or alternatively, a cyclodiene rhodium alkoxide complex.

In one aspect, the phosphine or the phosphine of the phosphine transition metal compound complex can be a monophosphine. Illustrative and non-limiting examples of monophosphines include an alkyl phosphine (e.g., trimethylphosphine, triethylphosphine, triisopropylphosphine, triadamantylphosphine, and the like), an aryl phosphine (e.g., triphenylphosphine, tri-p-tolylphosphine, and the like), or any combination thereof.

In another aspect, the phosphine or the phosphine of the phosphine transition metal compound complex can be a diphosphine having the following structure:

(I)

In structure (I), $L^1$ can be any suitable linking group or any linking group disclosed herein, and each R independently can be H or any $C_1$ to $C_{18}$ hydrocarbyl group, $C_1$ to $C_{18}$ hydrocarboxy group, or $C_1$ to $C_{18}$ hydrocarbylaminyl group disclosed herein. For instance, each R independently can be H or a $C_1$ to $C_{12}$ hydrocarbyl group; alternatively, H or a $C_1$ to $C_6$ hydrocarbyl group; alternatively, H or a $C_1$ to $C_{18}$ alkyl group, $C_2$ to $C_{18}$ alkenyl group, $C_6$ to $C_{18}$ aryl group, or $C_7$ to $C_{18}$ aralkyl group; or alternatively, H or a $C_1$ to $C_5$ alkyl group, $C_2$ to $C_5$ alkenyl group, $C_6$ to $C_8$ aryl group, or $C_7$ to $C_8$ aralkyl group. Each R independently in structure (I) can be, in certain aspects, H, a methyl group, an ethyl group, a propyl group, a butyl group, a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, a benzyl group, or a naphthyl group. In other aspects, each R independently can be H, a methyl group, an ethyl group, a propyl group, a butyl group, a pentyl group, a hexyl group, a heptyl group, an octyl group, a nonyl group, or a decyl group; alternatively, H, an ethenyl group, a propenyl group, a butenyl group, a pentenyl group, a hexenyl group, a heptenyl group, an octenyl group, a nonenyl group, or a decenyl group; or alternatively, H, a phenyl group, a tolyl group, a benzyl group, or a naphthyl group.

A hydrocarboxy group is used generically herein to include, for instance, alkoxy, aryloxy, aralkoxy, -(alkylene, arylene, or aralkylene)-O-(alkyl, aryl, or aralkyl) groups, and —O(CO)-(hydrogen or hydrocarbyl) groups, and these groups can comprise up to about 18 carbon atoms (e.g., $C_1$ to $C_{18}$, $C_1$ to $C_{10}$, or $C_1$ to $C_8$ hydrocarboxy groups). Cyclic groups also are included. Illustrative and non-limiting examples of hydrocarboxy groups can include, but are not limited to, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), a formate group, an acetate group, a stearate group, an oleate group, a benzoate group, a tetrahydrofuran group, a 1,4-dioxane group, and the like. In an aspect, the hydrocarboxy group which can be a R in formula (I) can be a methoxy group; alternatively, an ethoxy group; alternatively, an n-propoxy group; alternatively, an isopropoxy group; alternatively, an n-butoxy group; alternatively, a sec-butoxy group; alternatively, an isobutoxy group; alternatively, a tert-butoxy group; alternatively, an n-pentoxy group; alternatively, a 2-pentoxy group; alternatively, a 3-pentoxy group; alternatively, a 2-methyl-1-butoxy group; alternatively, a tert-pentoxy group; alternatively, a 3-methyl-1-butoxy group, alternatively, a 3-methyl-2-butoxy group; alternatively, a neo-pentoxy group; alternatively, a phenoxy group; alternatively, a toloxy group; alternatively, a xyloxy group; alternatively, a 2,4,6-trimethylphenoxy group; alternatively, a benzoxy group; alternatively, an acetylacetonate group; alternatively, a formate group; alternatively, an acetate group; alternatively, a stearate group; alternatively, an oleate group; alternatively, a benzoate group; alternatively, a tetrahydrofuran group; or alternatively, a 1,4-dioxane group.

The term hydrocarbylaminyl group is used generically herein to refer collectively to, for instance, alkylaminyl, arylaminyl, aralkylaminyl, dialkylaminyl, diarylaminyl, diaralkylaminyl, -(alkylene, arylene, or aralkylene)-N-(alkyl, aryl, or aralkyl) groups, and cyclic and aromatic amine groups (e.g., piperidine groups, pyrrole groups), and unless otherwise specified, the hydrocarbylaminyl groups can comprise up to about 18 carbon atoms (e.g., $C_1$ to $C_{18}$, $C_1$ to $C_{10}$, or $C_1$ to $C_8$ hydrocarbylaminyl groups). Accordingly, hydrocarbylaminyl is intended to cover both (mono)hydrocarbylaminyl and dihydrocarbylaminyl groups. In some aspects, the hydrocarbylaminyl group can be, for instance, a methylaminyl group (—NHCH$_3$), an ethylaminyl group (—NHCH$_2$CH$_3$), an n-propylaminyl group (—NHCH$_2$CH$_2$CH$_3$), an iso-propylaminyl group (—NHCH(CH$_3$)$_2$), an n-butylaminyl group (—NHCH$_2$CH$_2$CH$_2$CH$_3$), a t-butylaminyl group (—NHC(CH$_3$)$_3$), an n-pentylaminyl group (—NHCH$_2$CH$_2$CH$_2$CH$_2$CH$_3$), a neo-pentylaminyl group (—NHCH$_2$C(CH$_3$)$_3$), a phenylaminyl group (—NHC$_6$H$_5$), a tolylaminyl group (—NHC$_6$H$_4$CH$_3$), or a xylylaminyl group (—NHC$_6$H$_3$(CH$_3$)$_2$); alternatively, a methylaminyl group; alternatively, an ethylaminyl group; alternatively, a propylaminyl group; or alternatively, a phenylaminyl group. In other aspects, the hydrocarbylaminyl group which can be, for instance, a dimethylaminyl group (—N(CH$_3$)$_2$), a diethylaminyl group (—N(CH$_2$CH$_3$)$_2$), a di-n-propylaminyl group (—N(CH$_2$CH$_2$CH$_3$)$_2$), a di-isopropylaminyl group (—N(CH(CH$_3$)$_2$)$_2$), a di-n-butylaminyl group (—N(CH$_2$CH$_2$CH$_2$CH$_3$)$_2$), a di-t-butylaminyl group (—N(C(CH$_3$)$_3$)$_2$), a di-n-pentylaminyl group (—N(CH$_2$CH$_2$CH$_2$CH$_2$CH$_3$)$_2$), a di-neo-pentylaminyl group (—N(CH$_2$C(CH$_3$)$_3$)$_2$), a di-phenylaminyl group (—N(C$_6$H$_5$)$_2$), a di-tolylaminyl group (—N(C$_6$H$_4$CH$_3$)$_2$), or a di-xylylaminyl group (—N(C$_6$H$_3$(CH$_3$)$_2$)$_2$); alternatively, a dimethylaminyl group; alternatively, a di-ethylaminyl group; alternatively, a di-n-propylaminyl group; or alternatively, a di-phenylaminyl group.

In one aspect, the phosphine or the phosphine of the phosphine transition metal compound complex can comprise (or consist essentially of, or consist of) a 1,6-bis(dihydro-carbylphosphinyl)hexane, a substituted 1,6-bis(dihydrocarbylphosphinyl)hexane, a (1,3-phenylenedi-1,1-ethanediyl)bis(dihydrocarbylphosphine), a substituted (1,3-phenylenedi-1,1-ethanediyl)bis(dihydrocarbylphosphine), a 1,8-anthracenediylbis(dihydrocarbylphosphine), a substituted 1,8-anthracenediylbis(dihydrocarbylphosphine), a 1,8-tetradecahydroanthracenediylbis(dihydrocarbylphosphine), a substituted 1,8-tetradecahydroanthracenediylbis(dihydrocarbylphosphine), a (methylenedi-2,1-phenylene)bis(dihydrocarbylphosphine), a substituted (methylenedi-2,1-phenylene)bis(dihydrocarbylphosphine), a 9H-xanthene-4,5-diylbis(dihydrocarbylphosphine), or a substituted 9H-xanthene-4,5-diylbis(dihydrocarbylphosphine). For example, the phosphine or the phosphine of the phosphine transition metal compound complex can comprise (or consist essentially of, or consist of) a 1,6-bis(dihydrocarbylphosphinyl)hexane; alternatively, a substituted 1,6-bis(dihydrocarbylphosphinyl)hexane; alternatively, a (1,3-phenylenedi-1,1-ethanediyl)-bis(dihydrocarbylphosphine); alternatively, a substituted (1,3-phenylenedi-1,1-ethanediyl (bis-(dihydrocarbylphosphine); alternatively, a 1,8-anthracenediylbis(dihydrocarbylphosphine); alternatively, a substituted 1,8-anthracenediylbis(dihydrocarbylphosphine); alternatively, a 1,8-tetradecahydroanthracenediylbis(dihydrocarbylphosphine); alternatively, a substituted 1,8-tetradecahydroanthracenediylbis(dihydrocarbylphosphine); alternatively, a (methylenedi-2,1-phenylene)bis(dihydrocarbylphosphine); alternatively, a substituted (methylenedi-2,1-phenylene)bis(dihydrocarbylphosphine); alternatively, a 9H-xanthene-4,5-diylbis(dihydrocarbylphosphine); or alternatively, a substituted 9H-xanthene-4,5-diylbis(dihydrocarbylphosphine). Each hydrocarbyl independently can be any suitable hydrocarbyl group or any $C_1$ to $C_{18}$ hydrocarbyl group, $C_1$ to $C_{12}$ hydrocarbyl group, or $C_1$ to $C_6$ hydrocarbyl group disclosed herein.

In another aspect, the phosphine or the phosphine of the phosphine transition metal compound complex can comprise (or consist essentially of, or consist of) a 1,6-bisphosphinylhexane, a substituted 1,6-bisphosphinylhexane, a (1,3-phenylenedi-1,1-ethanediyl)bis(phosphine), a substituted (1,3-phenylenedi-1,1-ethanediyl)bis(phosphine), a 1,8-anthracenediylbis(phosphine), a substituted 1,8-anthracenediylbis(phosphine), a 1,8-tetradecahydroanthracenediylbis(phosphine), a substituted 1,8-tetradecahydroanthracenediylbis(phosphine), a (methylenedi-2,1-phenylene)bis(phosphine), a substituted (methylenedi-2,1-phenylene)bis(phosphine), a 9H-xanthene-4,5-diylbis(phosphine), or a substituted 9H-xanthene-4,5-diylbis(phosphine). For example, the phosphine or the phosphine of the phosphine transition metal compound complex can comprise (or consist essentially of, or consist of) a 1,6-bisphosphinylhexane; alternatively, a substituted 1,6-bisphosphinylhexane; alternatively, a (1,3-phenylenedi-1,1-ethanediyl)bis(phosphine); alternatively, a substituted (1,3-phenylenedi-1,1-ethanediyl)bis(phosphine); alternatively, a 1,8-anthracenediylbis(phosphine); alternatively, a substituted 1,8-anthracenediylbis(phosphine); alternatively, a 1,8-tetradecahydroanthracenediylbis(phosphine); alternatively, a substituted 1,8-tetradecahydroanthracenediylbis(phosphine); alternatively, a (methylenedi-2,1-phenylene)bis(phosphine); alternatively, a substituted (methylenedi-2,1-phenylene)bis(phosphine); alternatively, a 9H- xanthene-4,5-diylbis(phosphine); or alternatively, a substituted 9H-xanthene-4,5-diylbis(phosphine).

In yet another aspect, the phosphine or the phosphine of the phosphine transition metal compound complex can comprise (or consist essentially of, or consist of) a (9,9-dimethyl-9H-xanthen-4,5-diyl)bis(phosphine) or a substituted (9,9-dimethyl-9H-xanthen-4,5-diyl)bis(phosphine); alternatively, a (9,9-dimethyl-9H-xanthen-4,5-diylbis(phosphine); or alternatively, a substituted (9,9-dimethyl-9H-xanthen-4,5-diyl)bis(phosphine).

In still another aspect, the phosphine or the phosphine of the transition metal compound complex can have any one of the following structures, wherein Ph is a phenyl group, and each R independently can be H or any $C_1$ to $C_{18}$ hydrocarbyl group, $C_1$ to $C_{18}$ hydrocarboxy group, or $C_1$ to $C_{18}$ hydrocarbylaminyl group disclosed herein (e.g., H, a $C_1$ to $C_{12}$ hydrocarbyl group, a $C_1$ to $C_{12}$ hydrocarboxy group, or $C_1$ to $C_{12}$ hydrocarbylaminyl group; alternatively, H or a $C_1$ to $C_6$ hydrocarbyl group; alternatively, H or a $C_1$ to $C_{18}$ alkyl group, $C_2$ to $C_{18}$ alkenyl group, $C_6$ to $C_{18}$ aryl group, or $C_7$ to $C_{18}$ aralkyl group; or alternatively, H or a $C_1$ to $C_5$ alkyl group, $C_2$ to $C_5$ alkenyl group, $C_6$ to $C_8$ aryl group, or $C_7$ to $C_8$ aralkyl group):

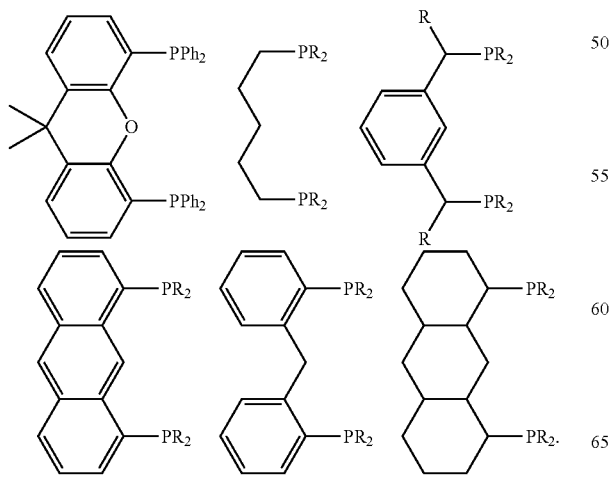

In another aspect, the phosphine or the phosphine of the transition metal compound complex can have any one of the following structures, wherein Ph is a phenyl group, Me is a methyl group, Ar is an aromatic group, each R independently can be H or any $C_1$ to $C_{18}$ hydrocarbyl group, $C_1$ to $C_{18}$ hydrocarboxy group, or $C_1$ to $C_{18}$ hydrocarbylaminyl group disclosed herein, and L can be any linking group disclosed herein.

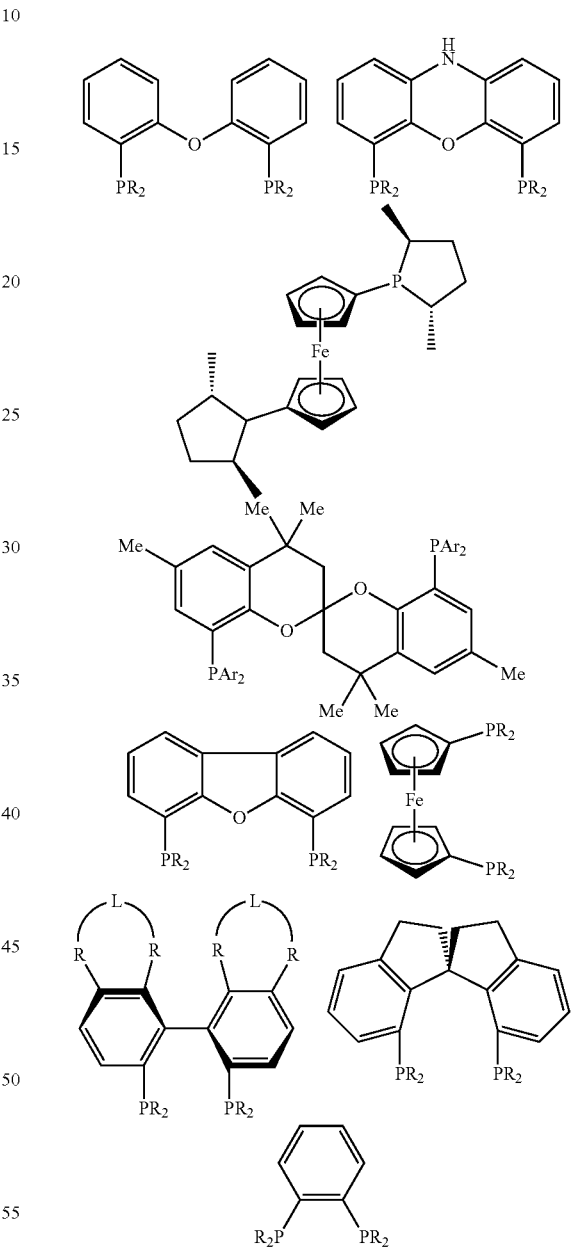

Any suitable linking group (L or $L^1$ in the above structures/formulas) can be used. For instance, the linking group can be any hydrocarbylene group (e.g., alkylene, cycloalkylene, or arylene), hydrocarboxy group (e.g., ether or cyclic ether), or hydrocarbylaminyl group disclosed herein.

The specific heteroatomic acid or heteroatomic acid derivative used in the catalyst composition is not particularly limited. In some aspects, the heteroatomic acid or heteroatomic acid derivative can comprise a carboxylic acid, an alcohol, a mineral acid, an ammonium salt, an amine, a thiol, and the like, as well as combinations thereof. For instance, the heteroatomic acid or heteroatomic acid derivative can comprise a carboxylic acid or carboxylic acid derivative. In one aspect, the carboxylic acid or carboxylic acid derivative can be an aliphatic carboxylic acid or carboxylic acid derivative, while in another aspect, the carboxylic acid or carboxylic acid derivative can be an aromatic carboxylic acid or carboxylic acid derivative. The carboxylic acid can be any suitable $C_1$ to $C_{24}$ carboxylic acid or any $C_1$ to $C_{24}$ carboxylic acid disclosed herein, either substituted or unsubstituted. Non-limiting examples of carboxylic acids can include formic acid, acetic acid, propionic acid, butanoic acid, pentanoic acid, hexanoic acid, stearic acid, acrylic acid, methacrylic acid, cinnamic acid, benzoic acid, salicylic acid, adipic acid, citric acid, or any combination thereof.

As used herein, "heteroatomic acid derivative" and "carboxylic acid derivative" are meant to encompass salts and esters of heteroatomic acids and carboxylic acids, respectively. For instance, the carboxylic acid derivative can be a carboxylic acid salt, a carboxylic acid ester, or any combination thereof; alternatively, a carboxylic acid salt; or alternatively, a carboxylic acid ester. Typical carboxylic acid salts can include alkali metal or alkaline earth metal salts (e.g., sodium, calcium, magnesium) of the carboxylic acid, while esters refers to compounds where at least one —OH group of the carboxylic acid is replaced by an alkoxy group (e.g., formates, acetates, hexanoates, stearates, acrylates, cinnamates, benzoates, and the like). Similar to the carboxylic acid, the carboxylic acid derivative can be any suitable $C_1$ to $C_{24}$ carboxylic acid derivative or any $C_1$ to $C_{24}$ carboxylic acid derivative disclosed herein, either substituted or unsubstituted. In an aspect, each substituent can be a $C_1$ to $C_8$ hydrocarbyl group, a $C_1$ to $C_5$ hydrocarbyl group, a $C_1$ to $C_8$ alkyl group, or a $C_1$ to $C_5$ alkyl group. In an aspect, the carboxylic acid ester can be a methyl ester, an ethyl ester, a propyl ester, or a butyl ester of any carboxylic acid described herein. As a representative example, the carboxylic acid or carboxylic acid derivative can comprise benzoic acid (or a substituted benzoic acid) or a salt or ester of benzoic acid (or a salt or ester of a substituted benzoic acid).

In circumstances where the catalyst composition comprises a transition metal compound, a phosphine, and a heteroatomic acid or heteroatomic acid derivative, the minimum molar ratio of the transition metal (of the transition metal compound) to the phosphine can be 0.2:1, 0.5:1, 0.8:1, or 0.95:1; additionally or alternatively, the maximum molar ratio of the transition metal to the phosphine can be 5:1, 4:1, 3:1, or 2.5:1. In an aspect, the transition metal (of the transition metal compound) to phosphine (or diphosphine) molar ratio can be in a range from any minimum transition metal to phosphine molar ratio disclosed herein to any maximum transition metal to phosphine molar ratio disclosed herein. In some non-limiting aspects, the molar ratio can be in a range from about 0.2:1 to about 5:1, from about 0.2:1 to about 3:1, from about 0.5:1 to about 4:1, or from about 0.95:1 to about 2.5:1. Other molar ratios of the transition metal to the phosphine (or diphosphine) are readily apparent from this disclosure.

The amount of the heteroatomic acid or heteroatomic acid derivative used in the catalyst composition is not particularly limited, but generally, the minimum molar ratio of the transition metal (of the transition metal compound or the phosphine transition metal compound complex) to the heteroatomic acid or heteroatomic acid derivative can be 0.8:1, 0.85:1, 0.9:1, or 0.95:1; additionally or alternatively, the maximum molar ratio of the transition metal to the heteroatomic acid or heteroatomic acid derivative can be 5:1, 3:1, 2:1, or 1.5:1. In an aspect, the transition metal (of the transition metal compound or the phosphine transition metal compound complex) to heteroatomic acid or heteroatomic acid derivative molar ratio can be in a range from any minimum transition metal to heteroatomic acid or heteroatomic acid derivative molar ratio disclosed herein to any maximum transition metal to heteroatomic acid or heteroatomic acid derivative molar ratio disclosed herein. In some non-limiting aspects, the molar ratio can be in a range from about 0.8:1 to about 5:1, from about 0.85:1 to about 3:1, from about 0.9:1 to about 2:1, or from about 0.95:1 to about 1.5:1. Other molar ratios of the transition metal (of the transition metal compound or the phosphine transition metal compound complex) to the heteroatomic acid or heteroatomic acid derivative are readily apparent from this disclosure.

Beneficially, the catalyst composition can further comprise an acceptor, also referred to as an acceptor olefin, which can increase the yield of the normal alpha olefin in the processes described in greater detail hereinbelow. In general, the acceptor can be any suitable compound having at least one carbon-carbon double bond. In an aspect, the acceptor can have at least 2 carbon atoms, at least 3 carbon atoms, at least 4 carbon atoms, or at least 5 carbon atoms. In some aspects, the acceptor can have a maximum of 100 carbon atoms, 80 carbon atoms, 60 carbon atoms, 50 carbon atoms, 40 carbon atoms, 30 carbon atoms, 25 carbon atoms, 20 carbon atoms, 15 carbon atoms, or 10 carbon atoms. Generally, the acceptor can have from any minimum number of carbon atoms described herein to any maximum number of carbon atoms described herein. For example, in some non-limiting aspects, the acceptor (or acceptor olefin) can have from 2 to 100 carbon atoms, from 3 to 80 carbon atoms, from 4 to 60 carbon atoms, or from 5 to 60 carbon atoms. Other carbon atom number ranges can be readily envisioned from the present disclosure and are encompassed herein. Mixtures or combinations of more than one acceptor (or acceptor olefin) can be employed in the present invention.

In an aspect, the acceptor (or acceptor olefin) can be a hydrocarbon compound or, alternatively, a heteroatomic compound. In some aspects, the acceptor can be aliphatic or, alternatively, aromatic. In other aspects, the acceptor can be acyclic or, alternatively, cyclic.

The acceptor can have at least one carbon-carbon double bond. In one aspect, the acceptor has from 1 to 10 double bonds; alternatively, from 1 to 8 double bonds; alternatively, from 3 to 5 double bonds; or alternatively, from 2 to 4 double bonds. In another aspect, the acceptor can have only one carbon-carbon double bond; alternatively, only two double bonds; alternatively, only three double bonds; alternatively, only four double bonds; alternatively, only five double bonds; or alternatively, only six double bonds.

Representative and non-limiting examples of acceptors (or acceptor olefins) having only one carbon-carbon double bond can comprise, consist essentially of, or consist of, either singly or in any combination, ethylene, t-butyl ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, 1-undecene, 1-dodecene, 1-tridecene, 1-tetradecene, 1-pentadecene, a vinylidene, or styrene.

Representative and non-limiting examples of cyclic acceptor olefins acceptor having only one carbon-carbon double bond can comprise, consist essentially of, or consist of, either singly or in any combination, norbornene, cyclopentene, cyclohexene, cycloheptene, or cyclooctene. In some aspects, cyclic acceptor olefins having only one carbon-carbon double bond can comprise, consist essentially of, or consist of, norbornene; alternatively, cyclopentene; alternatively, cyclohexene; alternatively, cycloheptene; or alternatively, cyclooctene.

Illustrative examples of acceptor olefins having at least two carbon-carbon double bonds that can be employed in the compositions and processes disclosed herein can comprise, consist essentially of, or consist of, either singly or in any combination, butadiene (1,3-butadiene), isoprene, 1,5-hexadiene, 1,7-octadiene, cyclobutadiene, cyclopentadiene, cyclohexadiene, cyclooctadiene, norbornadiene, vinylcyclohexene, vinylnorbornene, divinylbenzene, or cyclopentadiene dimer. Hence, mixtures or combinations of more than one acceptor olefin can be employed. Accordingly, the acceptor olefin having at least two double bonds can comprise, consist essentially of, or consist of, either singly or in any combination, butadiene, isoprene, 1,5-hexadiene, 1,7-octadiene, cyclobutadiene, cyclopentadiene, cyclohexadiene, or cyclooctadiene; alternatively, norbornadiene, vinylcyclohexene, vinylnorbornene, or divinylbenzene; alternatively, butadiene; alternatively, isoprene; alternatively, 1,5-hexadiene; alternatively, 1,7-octadiene; alternatively, cyclobutadiene; alternatively, cyclopentadiene; alternatively, cyclohexadiene; alternatively, cyclooctadiene; alternatively, norbornadiene; alternatively, vinylcyclohexene; alternatively, vinylnorbornene; alternatively, divinylbenzene; or alternatively, cyclopentadiene dimer.

In an aspect, the acceptor olefin can comprise, consist essentially of, or consist of, one or more compounds having only three carbon-carbon double bonds. Illustrative non-limiting examples of such compounds can comprise, consist essentially of, or consist of, singly or in any combination, trivinylcyclohexane, trivinylbenzene, cycloheptatriene, dimethyl heptatriene, octatriene, cyclooctatriene, or cyclododecatriene. In one aspect, the acceptor olefin can comprise, consist essentially of, or consist of, trivinylcyclohexane. In another aspect, the acceptor olefin can comprise, consist essentially of, or consist of, trivinylbenzene. In another aspect, the acceptor olefin can comprise, consist essentially of, or consist of, cycloheptatriene. In another aspect, the acceptor olefin can comprise, consist essentially of, or consist of, dimethyl heptatriene. In another aspect, the acceptor olefin can comprise, consist essentially of, or consist of, octatriene. Yet, in another aspect, the acceptor olefin can comprise, consist essentially of, or consist of, cyclooctatriene. In still another aspect, the acceptor olefin can comprise, consist essentially of, or consist of, cyclododecatriene. Additionally, the acceptor can comprise benzene and other aromatic compounds, as well as suitable 1,n-1,x-alkyltrienes (linear alkyltrienes).

Acceptor olefins having four or more carbon-carbon bonds also are contemplated. For instance, the acceptor olefin can comprise, consist essentially of, or consist of, cyclooctatetraene; alternatively, cyclododecatetraene; alternatively, a polybutadiene; or alternatively, a combination of two or more of these compounds.

In some aspects, the acceptor can comprise, consist essentially of, or consist of, an unsaturated triglyceride, while in other aspects, the acceptor can comprise, consist essentially of, or consist of, an unsaturated natural source oil. In an aspect, the acceptor can comprise, consist essentially of, or consist of, either singly or in any combination, soybean oil, corn oil, castor bean oil, or canola oil. In other aspects, the acceptor can comprise an unsaturated carboxylic acid, an ester of an unsaturated carboxylic acid (e.g., methyl, ethyl ester, propyl, or butyl ester), or any combination thereof alternatively, an unsaturated carboxylic acid; or alternatively, an ester of an unsaturated carboxylic acid. In some aspects, the unsaturated carboxylic acid, or the unsaturated carboxylic acid portion of the unsaturated carboxylic acid ester, which can be utilized as the aldehyde group acceptor can comprise, consist essentially of, or consist of, vinyl acetic acid, 3-pentenoic acid, maleic acid, fumaric acid, sorbic acid, caproleic acid, lauroleic acid, myristoleic acid, palmitoleic acid, oleic acid, ricinoleic acid, linoleic acid, linolenic acid, or any combination thereof. In yet another aspect, the acceptor can comprise an unsaturated carboxylic acid anhydride (e.g., maleic anhydride).

The acceptor also can comprise any suitable heteroatomic olefin compound, either singly or in combination. Representative and non-limiting examples of such heteroatomic olefin compounds include an enone, an enamine, an enol, an enamide (e.g., acrylamide), and the like, as well as combinations thereof.

Dehydroxymethylation and Dehydroformylation Processes

Aspects of this invention are directed to processes for producing normal alpha olefins from alcohols and aldehydes. A first process (a dehydroxymethylation process) consistent with this invention can comprise contacting a saturated linear $C_3$-$C_{36}$ hydrocarbon primary alcohol with any catalyst composition disclosed herein (e.g., transition metal compound, phosphine, heteroatomic acid or derivative, and acceptor) to form a $C_2$-$C_{35}$ normal alpha olefin (one carbon is removed in the conversion of the primary alcohol to the normal alpha olefin). A second process (a dehydroxymethylation process) consistent with this invention can comprise contacting a saturated linear $C_4$-$C_{36}$ hydrocarbon terminal vicinal diol with any catalyst composition disclosed herein to form a $C_2$-$C_{34}$ normal alpha olefin (two carbons are removed in the conversion of the diol to the normal alpha olefin). A third process (a dehydroformylation process) consistent with this invention can comprise contacting a saturated linear $C_3$-$C_{36}$ hydrocarbon aldehyde with any catalyst composition disclosed herein to form a $C_2$-$C_{35}$ normal alpha olefin (one carbon is removed in the conversion of the aldehyde to the normal alpha olefin). One or more than one alcohol, diol, or aldehyde can be used in these three processes. Generally, the features of the first process, the second process, and the third process (e.g., the normal alpha olefin, the catalyst system, the alcohol, the diol, the aldehyde, and the conditions under which the reaction is conducted, among other features) are independently described herein and these features can be combined in any combination to further describe these three processes. Moreover, additional process steps can be performed before, during, and/or after the steps of these processes, unless stated otherwise.

In the first process, the saturated linear hydrocarbon primary alcohol can be a $C_3$-$C_{36}$ alcohol; alternatively, a $C_3$-$C_{20}$ alcohol; or alternatively, a $C_5$-$C_{17}$ alcohol. In the second process, the saturated linear hydrocarbon terminal vicinal diol can be a $C_4$-$C_{36}$ diol; alternatively, a $C_4$-$C_{20}$ diol; or alternatively, a $C_6$-$C_{18}$ diol. In the third process, the saturated linear hydrocarbon aldehyde can be a $C_3$-$C_{36}$ aldehyde; alternatively, a $C_3$-$C_{20}$ aldehyde; or alternatively, a $C_5$-$C_{17}$ aldehyde. Thus, in certain aspects of this invention, the normal alpha olefin that can be produced can comprise a $C_2$-$C_{35}$ normal alpha olefin; alternatively, a $C_2$-$C_{34}$ normal alpha olefin; alternatively, a $C_2$-$C_{19}$ normal alpha olefin; alternatively, a $C_2$-$C_{18}$ normal alpha olefin; or alternatively, a $C_4$-$C_{16}$ normal alpha olefin.

In an aspect of this invention, the normal alpha olefin can comprise, consist essentially of, or consist of, ethylene, propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof; alternatively, 1-butene, 1-pentene, 1-hexene, 1-heptene, 1-octene, or any combination thereof or alternatively, 1-butene, 1-pentene, 1-hexene, or any combination thereof. In another aspect, the normal alpha olefin can comprise, consist essentially of, or consist of, 1-butene, 1-hexene, 1-octene, 1-decene, 1-dodecene, or any combination thereof. In yet another aspect, the normal alpha olefin can comprise, consist essentially of, or consist of, propylene; alternatively, 1-butene; alternatively, 1-pentene; alternatively, 1-hexene; alternatively, 1-heptene; alternatively, 1-octene; alternatively, 1-nonene; alternatively, 1-decene; alternatively, 1-dodecene; alternatively, 1-tetradecene; alternatively, 1-hexadecene; or alternatively, 1-octadecene.

The amount of the transition metal in the catalyst composition relative to the amount of the primary alcohol (or vicinal diol, or linear aldehyde) is not particularly limited. For instance, the minimum molar ratio of the primary alcohol (or vicinal diol, or linear aldehyde) to the transition metal (of the transition metal compound or the phosphine transition metal compound complex) can be 1:1, 2:1, 5:1, or 10:1; additionally or alternatively, the maximum molar ratio of the primary alcohol (or vicinal diol, or linear aldehyde) to the transition metal can be 10,000:1, 1000:1, 500:1, or 250:1. In an aspect, the primary alcohol (or vicinal diol, or linear aldehyde) to transition metal (of the transition metal compound or the phosphine transition metal compound complex) molar ratio can be in a range from any minimum molar ratio disclosed herein to any maximum molar ratio disclosed herein. In some non-limiting aspects, the molar ratio can be in a range from 1:1 to 10,000:1, from 2:1 to 1000:1, from 5:1 to 500:1, or from 10:1 to 250:1. Other molar ratios of the primary alcohol (or vicinal diol, or linear aldehyde) to transition metal are readily apparent from this disclosure. As those skilled in the art would readily recognize, the primary alcohol (or vicinal diol, or linear aldehyde) to transition metal molar ratio can change as the dehydroxymethylation or dehydroformylation reaction proceeds. Accordingly, these ranges of molar ratios are meant to encompass the initial ratio as well as any molar ratio of the primary alcohol (or vicinal diol, or linear aldehyde) to transition metal encountered as the dehydroxymethylation or dehydroformylation reaction proceeds.

In an aspect of this invention, the first process, the second process, and the third process can be conducted in the substantial absence of an acceptor (or an acceptor olefin)—i.e., the process can be conducted "acceptorless." Generally, in the substantial absence of an acceptor means that the formation of the normal alpha olefin is performed with less than 1, 0.5, 0.25, 0.1, 0.05, 0.025, or 0.01 mole % of an acceptor, based upon the amount of the primary alcohol (or vicinal diol, or linear aldehyde).

When used, the amount of the acceptor is not particularly limited. For instance, the normal alpha olefin can be formed at a minimum acceptor (or acceptor olefin) to primary alcohol (or vicinal diol, or linear aldehyde) molar ratio of 0.2:1, 0.5:1, 0.75:1, 1:1, 1.5:1, or 2:1; or additionally or alternatively, at a maximum acceptor to primary alcohol (or vicinal diol, or linear aldehyde) molar ratio of 1000:1, 500:1, 100:1, 50:1, 25:1, 10:1, or 5:1. In an aspect, the acceptor to primary alcohol (or vicinal diol, or linear aldehyde) molar ratio can be in a range from any minimum molar ratio disclosed herein to any maximum molar ratio disclosed herein. In some non-limiting aspects, the molar ratio can be in a range from 0.2:1 to 1000:1, from 0.5:1 to 500:1, from 0.75:1 to 100:1, from 1:1 to 10:1, or from 0.5:1 to 5:1. Other molar ratios of the acceptor to the primary alcohol (or vicinal diol, or linear aldehyde) are readily apparent from this disclosure. As those skilled in the art would readily recognize, the acceptor to primary alcohol (or vicinal diol, or linear aldehyde) molar ratio can change as the dehydroxymethylation or dehydroformylation reaction proceeds. Accordingly, these ranges of molar ratios are meant to encompass the initial reactant ratio as well as any molar ratio of the acceptor to the primary alcohol (or vicinal diol, or linear aldehyde) encountered as the dehydroxymethylation or dehydroformylation reaction proceeds.

The first process, second process, and third process for forming the normal alpha olefin can be conducted at a variety of temperatures, pressures, and time periods. For instance, the temperature at which the primary alcohol (or vicinal diol, or linear aldehyde) and the catalyst system (with or without acceptor) are initially combined can be the same as, or different from, the temperature at which the normal alpha olefin is formed. As an illustrative example, the primary alcohol (or vicinal diol, or linear aldehyde) and the catalyst system (with or without acceptor) can be initially charged or combined at temperature T1 and, after this initial charging of these materials, the temperature can be changed to a temperature T2 to allow for the reaction to proceed to form the normal alpha olefin. Likewise, the pressure can be varied throughout the process.

In an aspect, the first process, second process, and third process can be conducted and/or the normal alpha olefin can be formed at any suitable temperature. For instance, the first process, second process, and third process can be conducted and/or the normal alpha olefin can be formed at a minimum temperature of 0° C., 10° C., 15° C., or 20° C.; additionally or alternatively, at a maximum temperature of 150° C., 125° C., 100° C., or 75° C. In an aspect, the first process, second process, and third process can be conducted and/or the normal alpha olefin can be formed in a range from any minimum temperature disclosed herein to any maximum temperature disclosed herein. In some non-limiting aspects, the temperature can be in a range from 0° C. to 150° C.; alternatively, from 0° C. to 100° C.; alternatively, from 10° C. to 125° C.; alternatively, from 10° C. to 75° C.; alternatively, from 15° C. to 150° C.; alternatively, from 15° C. to 100° C.; alternatively, from 20° C. to 125° C.; or alternatively, from 20° C. to 75° C. Other temperature ranges are readily apparent from this disclosure. These temperature ranges also are meant to encompass circumstances where the first process, second process, and third process are conducted and/or the normal alpha olefin is formed at a series of different temperatures, instead of at a single fixed temperature, falling within the respective temperature ranges.

Generally, the first process, second process, and third process can be conducted and/or the normal alpha olefin can be formed at any suitable pressure, and this can vary depending upon the particular acceptor that is used (e.g., to maintain the acceptor in the liquid phase). For instance, the first process, second process, and third process can be conducted and/or the normal alpha olefin can be formed at a minimum pressure of 0 psig (0 kPa), 5 psig (34 kPa), or 10 psig (69 kPa); additionally or alternatively, at a maximum pressure of 2000 psig (13,785 kPa), 1000 psig (6,890 kPa), 750 psig (5,170 kPa), 500 psig (3,450 kPa), 250 psig (1,720 kPa), 150 psig (1,030 kPa), or 100 psig (689 kPa). In an aspect, the pressure can be in a range from any minimum pressure disclosed herein to any maximum pressure disclosed herein. While not being limited thereto, the first process, second process, and third process can be conducted and/or the second normal alpha olefin can be formed at a reaction pressure in a range from 0 to 2000 psig (0 to 13,785 kPa), from 10 to 2000 psig (69 to 13,785 kPa), from 0 to 1000 psig (0 to 6,890 kPa), from 5 to 1000 psig (34 to 6,890 kPa), from 5 to 750 psig (34 to 5,170 kPa), from 5 to 500 psig (34 to 3,450 kPa), from 5 to 250 psig (34 to 1,720 kPa), from 5 to 150 psig (34 to 1,030 kPa), or from 10 to 100 psig (69 to 689 kPa). Other reaction pressure ranges are readily apparent from this disclosure. In some aspects, the first process, second process, and third process can be conducted and/or the normal alpha olefin can be formed at atmospheric pressure, while in other aspects, the first process, second process, and third process can be conducted and/or the normal alpha olefin can be formed at sub-atmospheric pressures. These pressure ranges also are meant to encompass circumstances where the first process, second process, and third process are conducted and/or the normal alpha olefin is formed at a series of different pressures, instead of at a single fixed pressure, falling within the respective pressure ranges.

The first process, second process, and third process can be conducted in any suitable reactor or vessel in order to form the normal alpha olefin, non-limiting examples of which can include a fixed bed reactor, a stirred tank reactor, a plug flow reactor, a loop reactor, and a tubular reactor, including more than one reactor in series or in parallel, and including any combination of reactor types and arrangements. The first process, second process, and third process disclosed herein can be a batch process in some aspects, while in other aspects, the first process, second process, and third process can be a continuous process.

Consistent with an aspect of this invention, the first process, second process, and third process can be a continuous process and/or a flow process. For instance, the primary alcohol (or vicinal diol, or linear aldehyde)—and the acceptor—can contact a fixed bed of the catalyst composition at any suitable weight hourly space velocity (WHSV) and at any suitable targeted single pass conversion. Moreover, in a flow or continuous process, multi-passes can be used to increase the overall conversion of the primary alcohol (or vicinal diol, or linear aldehyde) to the normal alpha olefin.

In an aspect, the first process, second process, and third process can be conducted and/or the normal alpha olefin can be formed in a minimum reaction time of 5 minutes, 15 minutes, 45 minutes, or 1 hour; additionally or alternatively, in a maximum reaction time of 100 hours, 75 hours, 50 hours, 24 hours, 10 hours, or 5 hours. Generally, the first process, second process, and third process can be conducted and/or the normal alpha olefin can be formed in a time period ranging from any minimum reaction time disclosed herein to any maximum reaction time disclosed herein. In some non-limiting aspects, the reaction time can be in a range from 5 minutes to 100 hours; alternatively, from 15 minutes to 75 hours; alternatively, from 15 minutes to 50 hours; alternatively, from 45 minutes to 75 hours; alternatively, from 45 minutes to 24 hours; alternatively, from 1 hour to 24 hours; alternatively, from 1 hour to 10 hours; or alternatively, from 1 hour to 5 hours. Other reaction times are readily apparent from this disclosure. Depending upon the process and/or type of reactor used, the minimum reaction time, maximum reaction time, and reaction time range can be the average minimum reaction time, average maximum reaction time, and average reaction time range.

In particular aspects of this invention, the primary alcohol (or vicinal diol, or linear aldehyde) and the catalyst composition can be contacted in the absence of a solvent. However, in other aspects, the primary alcohol (or vicinal diol, or linear aldehyde) and the catalyst composition can be contacted in the presence of a solvent. Typically, when used, the solvent can be present in an amount up to 1,000 wt. %, based on the weight of the primary alcohol (or vicinal diol, or linear aldehyde). Alternatively, the primary alcohol (or vicinal diol, or linear aldehyde) and the catalyst system can be contacted in the presence of a solvent in an amount up 750 wt. %, up to 500 wt. %, up to 250 wt. %, up to 200 wt. %, up to 150 wt. %, or up to 100 wt. %. When a solvent is utilized, the minimum amount of solvent utilized can be at least 5 wt. %, at least 10 wt. %, at least 25 wt. %, at least 50 wt. %, or at least 75 wt. %, based on the weight of the primary alcohol (or vicinal diol, or linear aldehyde). Generally, the amount of solvent which can be utilized can range from any minimum amount of solvent disclosed herein to any maximum amount of solvent disclosed herein. In some non-limiting aspects, the primary alcohol (or vicinal diol, or linear aldehyde) and the catalyst system can be contacted in the presence of a solvent in an amount of from 5 wt. % to 1,000 wt. %, from 10 wt. % to 750 wt. %, from 25 wt. % to 500 wt. %, from 50 wt. % to 250 wt. %, from 50 wt. % to 150 wt. %, or from 75 wt. % to 125 wt. %, based on the weight of the primary alcohol (or vicinal diol, or linear aldehyde). Other solvent ranges are readily apparent from this disclosure.

As described herein, the primary alcohol (or vicinal diol, or linear aldehyde) and the catalyst composition can be contacted in the presence of a solvent. In one aspect, the solvent can comprise, consist essentially of, or consist of, a polar solvent, while in another aspect, the solvent can comprise, consist essentially of, or consist of, a hydrocarbon, a ketone, an alcohol, an ether, or any combination thereof. Hence, mixtures and/or combinations of solvents can be utilized in the normal alpha olefin synthesis processes disclosed herein.

In an aspect, the solvent employed in the first process, second process, and third process can comprise, consist essentially of, or consist of, a hydrocarbon solvent. Suitable hydrocarbon solvents can include, for example, aliphatic hydrocarbons (e.g., pentane, hexane, heptane, octane, decane, and combinations thereof) and aromatic hydrocarbons (e.g., benzene, toluene, xylene(s), ethylbenzene, and combinations thereof).

In an aspect, the solvent employed in the first process, second process, and third process can comprise, consist essentially of, or consist of, a ketone, an ether, or any combination thereof alternatively, a ketone; or alternatively, an ether. Suitable ketones or ethers include $C_2$ to $C_{20}$ ketones or ethers; alternatively, $C_2$ to $C_{10}$ ketones or ethers; or alternatively, $C_2$ to $C_5$ ketones or ethers. Non-limiting examples of suitable ketone solvents can include acetone, ethyl methyl ketone, or any combination thereof. Suitable ether solvents can be cyclic or acyclic, non-limiting examples of which can include dimethyl ether, diethyl ether, methyl ethyl ether, dibutylether, monoethers or diethers of glycols (e.g., a dimethyl glycol ether), glyme, diglyme, tetraglyme, furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an aspect, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group.

Consistent with aspects of this invention, the normal alpha olefin product can be isolated or separated from reaction by-products, residual reactants, catalyst systems components, and the like. As would be recognized by those skilled in the art, the normal alpha olefin product can be isolated or separated using any suitable technique, such as filtration, evaporation, distillation, or any combination of two or more of these techniques.

Generally, the yield of the normal alpha olefin (moles of normal alpha olefin based on the moles of the primary alcohol, vicinal diol, or linear aldehyde) in the first process, second process, and third process can be at least about 10%, at least about 20%, at least about 30%, at least about 40%, or at least about 50%. In certain aspects, the presence of an acceptor in the catalyst composition can unexpectedly and drastically improve the yield of the normal alpha olefin, while minimizing byproducts such as internal olefins. In such circumstances, the molar yield can be at least about 60%, at least about 70%, at least about 80%, at least about 90%, at least about 95%, at least about 98%, or at least about 99%. The amount of by-products, such as alkanes and internal olefins, formed by in the first process, second process, and third process can be less than about 20%, less than about 15%, less than about 10%, less than about 8%, less than about 5%, less than about 3%, less than about 2%, or less than about 1%. As above, these percentages are molar yields based on the initial amount of the primary alcohol (or vicinal diol, or linear aldehyde).

Selective Olefin Production Using Dehydroxymethylation

Aspects of this invention are directed to processes for producing normal alpha olefins via a linear primary alcohol or terminal vicinal diol. A fourth process (a multistep normal alpha olefin synthesis) consistent with this invention can comprise (i) conducting a hydroboration-oxidation reaction of a first normal alpha olefin having the structure $CH_3(CH_2)_nHC=CH_2$ to form a linear primary alcohol having the structure $CH_3(CH_2)_{n+1}CH_2OH$, and (ii) contacting the linear primary alcohol with any catalyst composition disclosed herein (e.g., transition metal compound, phosphine, heteroatomic acid or derivative, and acceptor) to form a second normal alpha olefin having the structure $CH_3(CH_2)_{n-1}HC=CH_2$ (one carbon is removed in the conversion of the first normal alpha olefin to the second normal alpha olefin). In the fourth process, n can be an integer ranging from 1 to 33. The fourth process also can be applied to a linear internal olefin, in which the double bond is chain-walked to the alpha position before undergoing the hydroboration-oxidation reaction. A fifth process (a multi-step normal alpha olefin synthesis) consistent with this invention can comprise (i) conducting a dihydroxylation reaction of a first normal alpha olefin having the structure $CH_3(CH_2)_nHC=CH_2$ to form a terminal vicinal diol having the structure $CH_3(CH_2)_nCH(OH)CH_2OH$, and (ii) contacting the terminal vicinal diol with any catalyst composition disclosed herein to form a second normal alpha olefin having the structure $CH_3(CH_2)_{n-2}HC=CH_2$ (two carbons are removed in the conversion of the first normal alpha olefin to the second normal alpha olefin). In the fifth process, n can be an integer ranging from 2 to 33. Generally, the features of the fourth process and the fifth process (e.g., the first normal alpha olefin, the second normal alpha olefin, the catalyst composition, the alcohol, the diol, and the conditions under which the dehydroxymethylation reaction is conducted, among other features) are independently described herein and these features can be combined in any combination to further describe these two processes. Moreover, additional process steps can be performed before, during, and/or after the steps of these processes, unless stated otherwise.

In the fourth process and fifth process, n can be an integer that can range from 1 to 33 and 2 to 33, respectively. In one aspect consistent with this invention, n can be an integer from 1 to 12, from 1 to 10, or from 1 to 7, in the fourth process, while in another aspect, n can be an integer from 2 to 12, from 2 to 10, or from 2 to 7, in the fifth process. Yet, in another aspect, n can be an integer from 3 to 10, and in still another aspect, n can be an integer from 4 to 9. For example, n can be equal to 2, equal to 3, equal to 4, equal to 5, and so forth. Accordingly, in some aspects, the second normal alpha olefin can comprise (or consist essentially of, or consist of) propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof; alternatively, 1-butene, 1-hexene, 1-octene, 1-decene, 1-dodecene, or any combination thereof; alternatively, 1-hexene, 1-octene, 1-decene, 1-dodecene, 1-tetradecene, or any combination thereof or alternatively, 1-hexene, 1-octene, 1-decene, or any combination thereof. In other aspects, the second normal alpha olefin can comprise (or consist essentially of, or consist of) 1-hexene; alternatively, 1-octene; or alternatively, 1-decene.

Referring now to step (i) of the fourth process, which is often referred to as a hydroboration-oxidation step, the process can comprise conducting a hydroboration-oxidation reaction of a first normal alpha olefin having the structure $CH_3(CH_2)_nHC=CH_2$ to form a linear primary alcohol having the structure $CH_3(CH_2)_{n+1}CH_2OH$. Stated another way, in this step, the first normal alpha olefin is subjected to a hydroboration-oxidation reaction to form a linear primary alcohol having the same number of carbon atoms as that of the first normal alpha olefin.

The hydroboration-oxidation step can be performed as described in U.S. Pat. Nos. 3,078,313, 3,358,034, and 3,439,046; Brown, H. C., Zweifel, G., (1959), "A Stereospecific cis Hydration of the Double Bond in Cyclic Derivatives," Journal of the American Chemical Society, 81:247; Brown, H.; Rao, B. C. (1957), "Communications—Selective Conversion of Olefins into Organoboranes Through Competitive Hydroboration, Isomerization and Displacement Reactions," Journal of Organic Chemistry, 22 (9):1137; Brewster, J. H., Negishi, E., Science 1980, 207, 44-46; Kabalka, G. W., Hedgecock, Jr, H. C., "Mild and convenient oxidation procedure for the conversion of organoboranes to the corresponding alcohols," J. Org. Chem. 1975, 40, 1776-1779; and Zweifel, G., Nagase, K., Brown, H. C., "Hydroboration. XIII. The hydroboration of dienes with disiamylborane. A convenient procedure for the conversion of selected dienes into unsaturated alcohols," J. Am. Chem. Soc. 1962, 84, 190-95, each of which is incorporated herein by reference in its entirety.

Suitable hydroboration-oxidation reaction conditions to convert the first normal alpha olefin having the structure $CH_3(CH_2)_nHC=CH_2$ to the linear primary alcohol having the structure $CH_3(CH_2)_{n+1}CH_2OH$ would be recognized by those skilled in the art in view of these references and the examples that follow.

Referring now to step (i) of the fifth process, which is often referred to as a dihydroxylation step, the process can comprise conducting a dihydroxylation reaction of a first normal alpha olefin having the structure $CH_3(CH_2)_n HC=CH_2$ to form a terminal vicinal diol having the structure $CH_3(CH_2)_n CH(OH)CH_2OH$. Stated another way, in this step, the first normal alpha olefin is subjected to a dihydroxylation reaction to form a terminal vicinal diol having the same number of carbon atoms as that of the first normal alpha olefin.

The dihydroxylation step can be performed as described in U.S. Pat. Nos. 3,582,270; 5,126,494; WO 89/06225; Vanrheenen, V., Kelly, R. C., Cha, D. Y., (1976) "An improved catalytic OsO4 oxidation of olefins to cis-1,2-glycols using tertiary amine oxides as the oxidant," Tetrahedron Lett. 17 (23):1973-1976; Eames, Jason, Mitchell, Helen J., Nelson, Adam, O'Brien, Peter, Warren, Stuart, Wyatt, Paul, (1999) "An efficient protocol for Sharpless-style racemic dihydroxylation," J. Chem. Soc., Perkin Trans. 1, 1999 (8):1095-1104; Jacobsen, E. N., Marko, I., Mungall, W. S., Schroeder, G., Sharpless, K. B., (1988), "Asymmetric dihydroxylation via ligand-accelerated catalysis," J. Am. Chem. Soc. 110 (6):1968-1970; Kolb, H. C., Van Nieuwenhze, M. S., Sharpless, K. B., (1994) "Catalytic Asymmetric Dihydroxylation," Chem. Rev. 94 (8):2483-2547; Ahrgren, Leif, Sutin, Lori, "Sharpless Asymmetric Dihydroxylation on an Industrial Scale," Org. Proc. Res. Dev., 1997, 1 (6), pp 425-427; and Johnson, Roy A., Sharpless, K. B., Catal. Asymmetric Synth. (1993), 227-22, each of which is incorporated herein by reference in its entirety.

Suitable dihydroxylation reaction conditions to convert the first normal alpha olefin having the structure $CH_3(CH_2)_n HC=CH_2$ to the terminal vicinal diol having the structure $CH_3(CH_2)_n CH(OH)CH_2OH$ would be recognized by those skilled in the art in view of these references and the examples that follow.

Referring now to step (ii) of the fourth process and the fifth process, which often is referred to as the dehydroxymethylation step. In this step, a linear primary alcohol (or terminal vicinal diol)—such as that formed in step (i)—can be contacted with any catalyst composition disclosed herein (e.g., transition metal compound, phosphine, heteroatomic acid or derivative, and acceptor) to form a second normal alpha olefin having the structure $CH_3(CH_2)_{n-1}HC=CH_2$ (from the linear primary alcohol with the loss of one carbon atom) or a second normal alpha olefin having the structure $CH_3(CH_2)_{n-2}HC=CH_2$ (from the terminal vicinal diol with the loss of two carbon atoms).

Step (ii) of the fourth process and the fifth process can be performed in the same manner as that described above for the first process, second process, and third process. Thus, any acceptor disclosed herein can be used, and the molar ratio of the acceptor to the linear alcohol (or vicinal diol) can be any amount in the range from about 0.2:1 to about 1000:1. Likewise, the molar ratio of the linear alcohol (or vicinal diol) to the transition metal of the transition metal compound or the phosphine transition metal compound complex (in the catalyst composition) can be any molar ratio in the range from about 2:1 to about 1000:1. Further, step (ii) can be performed in any solvent disclosed in relation to the first process, the second process, and the third process (e.g., toluene, THF, dioxane), and at any temperature (e.g., from about 0° C. to about 150° C.), pressure, WHSV or reaction time, and the second normal alpha olefin product can be isolated or separated from reaction by-products, residual reactants, catalyst systems components, and the like using any suitable technique.

Generally, the yield of the second normal alpha olefin (moles of second normal alpha olefin based on the moles of the alcohol or diol) in step (ii) of the fourth process or fifth process can be at least about 10%, at least about 20%, at least about 30%, at least about 40%, or at least about 50%. In certain aspects, the presence of an acceptor in the catalyst composition can unexpectedly and drastically improve the yield of the second normal alpha olefin, while minimizing byproducts such as internal olefins. In such circumstances, the molar yield can be at least about 60%, at least about 70%, at least about 80%, at least about 90%, at least about 95%, at least about 98%, or at least about 99%. The amount of by-products, such as alkanes and internal olefins, formed in step (ii) of the fourth process and fifth process can be less than about 20%, less than about 15%, less than about 10%, less than about 8%, less than about 5%, less than about 3%, less than about 2%, or less than about 1%. These percentages are molar yields based on the initial amount of the alcohol or diol.

Selective Olefin Production Using Dehydroformylation

Aspects of this invention are directed to processes for producing normal alpha olefins via a linear aldehyde. A sixth process consistent with this invention can comprise (or consist essentially of, or consist of) (i) contacting a first normal alpha olefin having the structure $CH_3(CH_2)_n HC=CH_2$ and a metathesis catalyst system to form a linear internal olefin having the structure $CH_3(CH_2)_n HC=CH(CH_2)_n CH_3$, (ii) contacting the linear internal olefin with a hydroformylation catalyst system, carbon monoxide, and hydrogen to form a linear aldehyde having the formula $CH_3(CH_2)_{2n+3}C(=O)H$, and (iii) contacting the linear aldehyde with any catalyst composition disclosed herein (e.g., transition metal compound, phosphine, heteroatomic acid or derivative, and acceptor) to form a second normal alpha olefin having the structure $CH_3(CH_2)_{2n+1}HC=CH_2$. In the sixth process, n can be an integer that can range from 0 to 15. Generally, the features of the sixth process (e.g., the first normal alpha olefin, the metathesis catalyst, the linear internal olefin, the hydroformylation catalyst system, the catalyst composition, the second normal olefin, and the conditions under which each of the steps are conducted, among other features) are independently described herein and these features can be combined in any combination to further describe the sixth normal alpha olefin synthesis process. Moreover, additional process steps can be performed before, during, and/or after any of the steps of any of the processes disclosed herein, unless stated otherwise.

In this multistep process, n can be an integer that can range from 0 to 15. In one aspect consistent with this invention, n can be an integer from 0 to 10, while in another aspect, n can be an integer from 0 to 7. Yet, in another aspect, n can be an integer from 1 to 7, and in still another aspect, n can be an integer from 1 to 5. For example, n can be equal to 1, equal to 2, equal to 3, equal to 4, and so forth.

In some aspects of this invention, the first normal alpha olefin can comprise, consist essentially of, or consist of, propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof; alternatively, 1-butene, 1-pentene, 1-hexene, 1-heptene, 1-octene, or any combination thereof; or alternatively, 1-butene, 1-pentene, 1-hexene, or any combination thereof. In further aspects, the first normal alpha olefin can comprise, consist essentially of, or consist of, propylene; alternatively, 1-butene; alternatively, 1-pentene; alternatively, 1-hexene; alternatively, 1-heptene; alternatively, 1-octene; alternatively, 1-nonene; alternatively, 1-decene; alternatively, 1-dodecene; alternatively, 1-tetradecene; alternatively, 1-hexadecene; or alternatively, 1-octadecene.

In one aspect of this invention, the first normal alpha olefin can comprise (or consist essentially of, or consist of) 1-butene, and the second normal alpha olefin can comprise (or consist essentially of, or consist of) 1-hexene. In another aspect of this invention, the first normal alpha olefin can comprise (or consist essentially of, or consist of) 1-pentene, and the second normal alpha olefin can comprise (or consist essentially of, or consist of) 1-octene. In yet another aspect of this invention, the first normal alpha olefin can comprise (or consist essentially of, or consist of) 1-hexene, and the second normal alpha olefin can comprise (or consist essentially of, or consist of) 1-decene.

The integer n, the first normal alpha olefin, and the second normal alpha olefin are described herein and their features can be utilized without limitation to further describe the sixth normal alpha olefin synthesis process disclosed herein. Other suitable values for the integer n and selections for the first normal alpha olefin and the second normal alpha olefin are readily apparent from this disclosure.

Step (i) of the sixth process often is referred to as the metathesis step, and in this step, the first normal alpha olefin having the structure $CH_3(CH_2)_nHC=CH_2$ can be contacted with a metathesis catalyst system to form a linear internal olefin having the structure $CH_3(CH_2)_nHC=CH(CH_2)_nCH_3$.

Any suitable metathesis catalyst system can be used in the metathesis step, non-limiting examples of which can include a metal oxide based metathesis catalyst system, a metal halide based metathesis catalyst system, a metal carbene based metathesis catalyst system, or any combination thereof. In one aspect, the metathesis catalyst system can be a metal oxide based metathesis catalyst system or a metal halide based metathesis catalyst system, while in another aspect, the metathesis system catalyst can be a metal oxide based metathesis catalyst system; alternatively, a metal halide based metathesis catalyst system; or alternatively, a metal carbene based metathesis catalyst system.

Metal oxide based metathesis catalyst systems can comprise (or consist essentially of, or consist of) cobalt oxide, molybdenum oxide, tungsten oxide, rhenium oxide, or any combination thereof. For instance, the metal oxide based catalyst system can comprise (or consist essentially of, or consist of) cobalt oxide; alternatively, molybdenum oxide; alternatively, tungsten oxide; or alternatively, rhenium oxide. Optionally, the metal oxide based metathesis catalyst system can further comprise a support, or a metal alkyl activator, or both a support and a metal alkyl activator. Illustrative supports can include alumina, silica, silica-alumina, and aluminum-phosphate, amongst other solid oxide materials. Accordingly, non-limiting examples of supported metal oxide based metathesis catalyst systems can include molybdenum oxide on alumina ($MoO_3/Al_2O_3$), tungsten oxide on silica ($WO_3/SiO_2$), rhenium oxide on alumina ($Re_2O_7/Al_2O_3$), cobalt oxide and molybdenum oxide on alumina ($CoO/MoO_3/Al_2O_3$), and rhenium oxide on alumina activated with tetramethyl tin ($Re_2O_7/Al_2O_3SnMe_4$). Other suitable metal oxide based metathesis catalyst systems are known to those skilled in the art.

Further, the metal oxide based metathesis catalyst system can include a metal alkyl activator, which can include alkyl lithium, alkyl magnesium, alkyl aluminum, alkyl tin compounds, or any mixture thereof. In an aspect, the metal alkyl activator can be an alkyl lithium compound. In another aspect, the metal alkyl activator can be an alkyl magnesium compound. In another aspect, the metal alkyl activator can be an alkyl aluminum compound. In yet another aspect, the metal alkyl activator can be an alkyl tin compound. Non-limiting examples of alkyl aluminum compounds can include trialkyl aluminum compounds and/or alkyl aluminum halide compounds. The alkyl groups on the metal alkyl activator can include any $C_1$ to $C_{10}$ hydrocarbyl group, or alternatively, any $C_1$ to $C_5$ hydrocarbyl group. In various aspects, the alkyl group for the metal alkyl activator can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group; alternatively, an n-butyl group; alternatively, a sec-butyl group; or alternatively, a tert-butyl group. Representative examples of suitable trialkyl aluminum compounds can include trimethylaluminum, triethylaluminum, and triisobutylaluminum. The halide of the alkyl aluminum halide compound can be chloride, bromide, or iodide; alternatively, chloride; alternatively, bromide; or alternatively, iodide. Examples of suitable alkyl aluminum halide compounds can include ethylaluminum dichloride, diethylaluminum chloride, and ethylaluminum sesquichloride. Suitable and non-limiting examples of alkyl tin compounds can include tetramethyl tin, tetraethyl tin, and tetrabutyl tin.

Metal halide based metathesis catalyst systems can comprise (or consist essentially of, or consist of) a halide of tungsten, a halide of molybdenum, or a combination thereof. For instance, the metal halide based metathesis catalyst system can comprise (or consist essentially of, or consist of) a halide of tungsten, or alternatively, a halide of molybdenum. The halide of the metal halide based metathesis catalyst system can be chloride, bromide, or iodide. In one aspect, the halide can be chloride, and in another aspect, the halide can be bromide, and in yet another aspect, the halide can be iodide. Hence, the metal halide based metathesis catalyst system can comprise (or consist essentially of, or consist of) tungsten chloride, molybdenum chloride, or a mixture thereof; alternatively, tungsten chloride; or alternatively, molybdenum chloride.

Optionally, the metal halide based metathesis catalyst system can further comprise a metal alkyl activator (as described herein), oxygen, an alcohol, or any combination thereof, alternatively, a metal alkyl activator; alternatively, oxygen; or alternatively, an alcohol. Non-limiting examples of metal halide based metathesis catalyst systems can include tungsten chloride/tetrabutyl tin ($WCl_6/SnMe_4$), tungsten chloride/ethylaluminum dichloride ($WCl_6/EtAlCl_2$), tungsten chloride/ethylaluminum dichloride/ethyl alcohol ($WCl_6/EtAlCl_2/EtOH$), molybdenum chloride/triethyl aluminum ($MoCl_5/AlEt_3$), and molybdenum chloride/triethyl aluminum/$O_2$ ($MoCl_5/AlEt_3/O_2$). Other suitable metal halide based metathesis catalyst systems are known to those skilled in the art.

Metal carbene based metathesis catalyst systems can comprise (or consist essentially of, or consist of) tungsten, tantalum, osmium, molybdenum, ruthenium, or any combination thereof. For instance, the metal carbene based metathesis catalyst system can comprise (or consist essentially of, or consist of) tungsten; alternatively, tantalum; alternatively, osmium; alternatively, molybdenum; or alternatively, ruthenium. These metal carbene based metathesis catalyst systems can contain compounds which have a stable metal-carbon double bond or can form a metal-carbon double bond in situ from a metal precursor having a stable metal-carbon single bond.

In an aspect, a ruthenium carbene based metathesis catalyst system can comprise a compound having the structure $L^1L^2X_2Ru=CHR^1$, wherein $L^1$ and $L^2$ can be an organic ligand, X can be a halide, and $R^1$ can be hydrogen or a hydrocarbyl group. Generally, the compound in the ruthenium carbene based metathesis catalyst system having the structure $L^1L^2X_2Ru=CHR^1$ can be described using any combination of $L^1$, $L^2$, X, or $R^1$ described herein.

Generally, $L^1$ and $L^2$ independently can be $R'_3P$, an imidazolinylidene group, or an imidazolidinylidene group. In some aspects, $L^1$ and $L^2$ can be $R'_3P$; alternatively, $L^1$ can be $R'_3P$ and $L^2$ can be an imidazolinylidene group or an imidazolidinylidene group; alternatively, $L^1$ can be $R'_3P$ and $L^2$ can be an imidazolinylidene group; alternatively, $L^1$ can be $R'_3P$ and $L^2$ can be an imidazolidinylidene group; alternatively, $L^1$ and $L^2$ can be imidazolinylidene groups; or alternatively, $L^1$ and $L^2$ can be imidazolidinylidene groups. In aspects of this invention, R' can be a hydrocarbyl group, where each R' of $R'_3P$ can be the same; alternatively, each R' of $R'_3P$ can be different; or alternatively, one R' of $R'_3P$ can be different from the other two R' groups. In some aspects, each R' of $R'_3P$ independently can be a $C_1$ to $C_{15}$ hydrocarbyl group; or alternatively, a $C_1$ to $C_{10}$ hydrocarbyl group. In other aspects, each hydrocarbyl R' of $R'_3P$ independently can be an alkyl group or an aromatic group; alternatively, an alkyl group; or alternatively, an aromatic group. In an aspect, each alkyl R' of $R'_3P$ independently can be a methyl group, ethyl group, n-propyl group, isopropyl group, tert-butyl group, neo-pentyl group, cyclopentyl group, or cyclohexyl group. In some aspects, one or more R' groups of $R'_3P$ can be a phenyl group, or alternatively, a substituted phenyl group. In an aspect, the substituents of any substituted phenyl group independently can be a $C_1$-$C_5$ organyl group, or alternatively, a $C_1$-$C_5$ hydrocarbyl group. In some aspects, $R'_3P$ can be a trialkyl phosphine or triphenyl phosphine; alternatively, a trialkyl phosphine; or alternatively, triphenyl phosphine. In an aspect, $R'_3P$ can be trimethyl phosphine, triethyl phosphine, triisopropyl phosphine, tri-tert-butyl phosphine, tri-neopentyl phosphine, tricyclopentyl phosphine, tricyclohexyl phosphine, or triphenyl phosphine; alternatively, triisopropyl phosphine, tri-tert-butyl phosphine, tri-neopentyl phosphine, tricyclopentyl phosphine, tricyclohexyl phosphine, or triphenyl phosphine; alternatively, tricyclopentyl phosphine, tricyclohexyl phosphine, or triphenyl phosphine; alternatively, tricyclopentyl phosphine or tricyclohexyl phosphine; alternatively, tricyclopentyl phosphine; alternatively, tricyclohexyl phosphine; or alternatively triphenyl phosphine.

In an aspect, the imidazolinylidene group or imidazolidinylidene group can be a $C_3$ to $C_{80}$ imidazolinylidene group or imidazolidinylidene group; alternatively, a $C_3$ to $C_{50}$ imidazolinylidene group or imidazolidinylidene group; or alternatively, a $C_5$ to $C_{40}$ imidazolinylidene group or imidazolidinylidene group. In some aspects, the imidazolinylidene group can be a 1,3-disubstituted imidazolinylidene group. In some aspects, the imidazolidinylidene group can be a 1,3-disubstituted imidazolidinylidene group. In an aspect, the 1,3-substituents of the 1,3-disubstituted imidazolinylidene group or 1,3-disubstituted imidazolidinylidene group independently can be any suitable hydrocarbyl group. In an aspect, the 1,3-substituents of the 1,3-disubstituted imidazolinylidene group or 1,3-disubstituted imidazolidinylidene group independently can be a $C_1$ to $C_{30}$ hydrocarbyl group. In some aspects, the 1,3-substituents of the 1,3-disubstituted imidazolinylidene group or 1,3-disubstituted imidazolidinylidene group independently can be a $C_6$ to $C_{20}$ aromatic group or a $C_1$ to $C_{10}$ alkyl group. In other aspects, the 1,3-substituents of the 1,3-disubstituted imidazolinylidene group or 1,3-disubstituted imidazolidinylidene group independently can be a $C_6$ to $C_{20}$ aromatic group, or alternatively, a $C_1$ to $C_{10}$ alkyl group. In an aspect, each aromatic group of the 1,3-disubstituted imidazolinylidene group or 1,3-disubstituted imidazolidinylidene group independently can be a substituted aromatic group. In some aspects, the substituted aromatic group of the 1,3-disubstituted imidazolinylidene group or 1,3-disubstituted imidazolidinylidene group can be a 2-disubstituted phenyl group, a 2,6-disubstituted phenyl group, or a 2,4,6-trisubstituted phenyl group; alternatively, a 2,6-disubstituted phenyl group; or alternatively, a 2,4,6-trisubstituted phenyl group. Suitable substituents for any substituted phenyl group within the 1,3-disubstituted imidazolinylidene group or 1,3-disubstituted imidazolidinylidene group can include any $C_1$ to $C_{10}$ hydrocarbyl group, or alternatively, any $C_1$ to $C_5$ hydrocarbyl group. In some aspects, each hydrocarbyl substituent independently can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group, alternatively, an isopropyl group; or alternatively, a tert-butyl group. In some aspects, each substituted aromatic group of the 1,3-disubstituted imidazolinylidene group or 1,3-disubstituted imidazolidinylidene group independently can be a 2,6-diisopropylphenyl group or a 2,4,6-trimethylphenyl group; alternatively, a 2,6-diisopropylphenyl group; or alternatively, a 2,4,6-trimethylphenyl group.

In various aspects, each X of the compound having the structure $L^1L^2X_2Ru=CHR^1$ independently can be chloride, bromide, or iodide. In an aspect, X can be chloride. In another aspect, X can be bromide. In yet another aspect, X can be iodide. $R^1$ of the compound having the structure $L^1L^2X_2Ru=CHR^1$ can be hydrogen or a $C_1$ to $C_{20}$ hydrocarbyl group. In some aspects, $R^1$ can be a methyl group, an ethyl group, an isopropyl group, a tert-butyl group, a phenyl group, a 2-methyl-2-propene group, or a 2,2-diphenylethene group. In other aspects, $R^1$ can be a tert-butyl group, a phenyl group, a 2-methyl-2-propene group, or a 2,2-diphenylethene group; alternatively, hydrogen; alternatively, a tert-butyl group; alternatively, a phenyl group; alternatively, a tert-butyl group; alternatively, a phenyl group; alternatively, a 2-methyl-2-propene group; or alternatively, a 2,2-diphenylethene group.

In some non-limiting aspects, the ruthenium carbene based metathesis catalyst system can comprise dichloro (phenylmethylene) bis(tricyclohexyl phosphine) ruthenium, dichloro(3-methyl-2-butenylidene) bis(tricyclohexyl phosphine) ruthenium, dichloro(3-methyl-2-butenylidene) bis (tricyclopentyl phosphine) ruthenium, 1,3-bis-(2,4,6-trimethylphenyl)-2-(imidazolidinylidene)(phenylmethylene) dichloro(tricyclohexyl phosphine) ruthenium, or 1,3-bis-(2, 6-diisopropylphenyl)-2-(imidazolidinydene) (phenylmethylene)dichloro(tricyclohexyl phosphine) ruthenium. In some aspects, the ruthenium carbene based metathesis catalyst system can comprise dichloro(phenylmethylene) bis(tricyclohexyl phosphine) ruthenium; alternatively, dichloro(3-methyl-2-butenylidene) bis(tricyclohexyl phosphine) ruthenium; alternatively, 1,3-bis-(2,4,6-trimethylphenyl)-2-(imidazolidinylidene)(phenylmethylene)dichloro(tricyclohexyl phosphine) ruthenium; or alternatively, 1,3-bis-(2,6-diisopropylphenyl)-2-(imidazolidinylidene)(phenylmethylene)dichloro(tricyclohexyl phosphine) ruthenium.

In an aspect, a molybdenum carbene based metathesis catalyst system can comprise a compound having the structure $Mo(=CHR^2)(NAr)(OR^3)_2$, wherein $R^2$ is a hydrogen or hydrocarbyl group, Ar is a substituted aromatic ring, and $R^3$ is a hydrocarbyl group or a halogenated hydrocarbyl group. Generally, the compound in the molybdenum carbene based metathesis catalyst system having the structure $Mo(=CHR^2)(NAr)(OR^3)_2$ can be described using any combination of $R^2$, Ar, and $R^3$ described herein.

In some aspects, $R^2$ of the compound having the structure $Mo(=CHR^2)(NAr)(OR^3)_2$ can be hydrogen or a $C_1$ to $C_{20}$ hydrocarbyl group, or alternatively, a $C_1$ to $C_{20}$ hydrocarbyl group. In some aspects, $R^2$ can be a methyl group, an ethyl group, an isopropyl group, a tert-butyl group, a phenyl group, a 2-methyl-2-propene group, or a 2,2-diphenylethene group. In other aspects, $R^2$ can be a tert-butyl group, a phenyl group, a 2-methyl-2-propene group, or a 2,2-diphenylethene group; alternatively, a tert-butyl group or a phenyl group; alternatively, hydrogen; alternatively, a tert-butyl group; alternatively, a phenyl group; alternatively, a 2-methyl-2-propene group; or alternatively, a 2,2-diphenylethene group.

In an aspect, the substituted aromatic ring, Ar, of the compound having the structure $Mo(=CHR^2)(NAr)(OR^3)_2$ can be a $C_6$ to $C_{30}$ aromatic group, or alternatively, a $C_6$ to $C_{20}$ aromatic group. In some aspects, each substituent of the substituted aromatic ring, Ar, independently can be a $C_6$ to $C_{20}$ hydrocarbyl group, a $C_1$ to $C_{10}$ hydrocarbyl group, or a $C_1$ to $C_5$ hydrocarbyl group. In some aspects, the substituted aromatic ring, Ar, can be a 2-substituted phenyl group, a 2,6-disubstituted phenyl group, or a 2,4,6-trisubstituted phenyl group. In an aspect, each substituent of the substituted aromatic ring independently can be a methyl group, an ethyl group, an isopropyl group, a tert-butyl group, or a neopentyl group; alternatively, a methyl group, an isopropyl group, or a tert-butyl group; alternatively, a methyl group or an isopropyl group. In some aspects, each substituent of the substituted aromatic ring independently can be a methyl group; alternatively, an isopropyl group; or alternatively, a tert-butyl group. In some non-limiting aspects, the substituted aromatic ring, Ar, can be a 2-tert-butylphenyl group, a 2,6-dimethylphenyl group, a 2,6-diisopropylphenyl group, or a 2,4,6-trimethyl phenyl group; alternatively, a 2-tert-butylphenyl group; alternatively, a 2,6-dimethylphenyl group; alternatively, a 2,6-diisopropylphenyl group; or alternatively, a 2,4,6-trimethyl phenyl group.

In an aspect, each $R^3$ of the compound having the structure $Mo(=CHR^2)(NAr)(OR^3)_2$ independently can be a $C_1$ to $C_{10}$ organic group, or alternatively, a $C_1$ to $C_5$ organic group. In some aspects, the $C_1$ to $C_{10}$ or $C_1$ to $C_5$ organic group can be a hydrocarbylhalyl group (a group consisting of hydrogen, carbon, and halogen atoms); alternatively, a hydrocarbylfluoryl group (a group consisting of hydrogen, carbon, and fluorine atoms); or alternatively, a hydrocarbyl group. In an aspect, the halogen atoms of the hydrocarbylhalyl group can be fluorine, chlorine, bromine, iodine, or any combination thereof; alternatively, fluorine; alternatively, chlorine; alternatively, bromine; or alternatively, iodine. In some aspects, each $R^3$ independently can be a tert-butyl group or a hexafluoro-tert-butyl group. In other aspects, $(OR^3)_2$ can represent a single organic group wherein the two $R^3$ groups attached to the oxygen atoms are connected via a bond between any divalent, trivalent, or tetravalent atom within the $R^3$ groups. In further aspects, $(OR^3)_2$ can represent a single organic group wherein the two $R^3$ groups attached to the oxygen atoms are connected via a carbon-carbon bond between any carbon atom of the two $R^3$ groups.

In an aspect, the molybdenum carbene based metathesis catalyst system can comprise $Mo(=CH—C(CH_3)_3)(N-2,6-diisopropylphenyl)(OC(CH_3)_3)$, $Mo(=CH—C(CH_3)_2(C_6H_5))(N-2,6-diisopropylphenyl)(OC(CH_3)_3)$, $Mo(=CH—C(CH_3)_3)(N-2,6-diisopropylphenyl)-(OC(CH_3)(CF_3)_2)$, or $Mo(=CH—C(CH_3)_2(C_6H_5))(N-2,6-diisopropylphenyl)(OC(CH_3)(CF_3)_2)$. In other aspects, the molybdenum carbene based metathesis catalyst system can comprise $Mo(=CH—C(CH_3)_3)(N-2,6-diisopropylphenyl)(OC(CH_3)_3)$; alternatively, $Mo(=CH—C(CH_3)_2(C_6H_5))(N-2,6-diisopropylphenyl)(OC(CH_3)_3)$; alternatively, $Mo(=CH—C(CH_3)_3)(N-2,6-diisopropylphenyl)(OC(CH_3)(CF_3)_2)$; or alternatively, $Mo(=CH—C(CH_3)_2(C_6H_5))(N-2,6-diisopropylphenyl)(OC(CH_3)(CF_3)_2)$.

Optionally, the metal carbene based metathesis catalyst system can further comprise a support. Illustrative supports can include alumina, silica, silica-alumina, and aluminum-phosphate, amongst other solid oxide materials. Additionally, the support can comprise a polymer, and the metal carbene metathesis catalyst compound can be tethered to the support via any of the ligands which do not contain the metal-carbon double bond.

Any suitable conditions for the metathesis step can be employed, as would be recognized by those skilled in the art in view of this disclosure and the examples that follow, and U.S. Pat. No. 8,765,984.

Referring now to step (ii) of the sixth process, which often is referred to as the hydroformylation step. In this step, a linear internal olefin—such as that formed in the metathesis step—can be contacted with a hydroformylation catalyst system, carbon monoxide, and hydrogen to form a linear aldehyde having the formula $CH_3(CH_2)_{2n+3}C(=O)H$. As described herein, n can be an integer ranging from 0 to 15; for example, n can be an integer from 0 to 10, n can be an integer from 0 to 7, n can be an integer from 1 to 7, or n can be an integer from 1 to 5.

Consistent with certain aspects of this invention, step (ii) can comprise contacting the linear internal olefin with a hydroformylation catalyst system and syngas (also referred to as synthesis gas) to form the linear aldehyde. As would be recognized by those skilled in the art, syngas is a mixture containing predominately carbon monoxide and hydrogen. Syngas also can contain carbon dioxide and methane in lesser amounts.

Any suitable hydroformylation catalyst system can be used in the hydroformylation step, non-limiting examples of which can include a rhodium compound, a cobalt compound, a ruthenium compound, an iridium compound, a platinum compound, a palladium compound, an iron compound, or any combination thereof. For instance, the hydroformylation catalyst system can comprise a rhodium compound; alternatively, a cobalt compound; alternatively, a ruthenium compound; alternatively, an iridium compound; alternatively, a platinum compound; alternatively, a palladium compound; or alternatively, an iron compound.

Any suitable conditions for the hydroformylation step can be employed, as would be recognized by those skilled in the art in view of this disclosure, and in particular, the examples that follow.

Referring now to step (iii) of the sixth process, which often is referred to as the dehydroformylation step. In this step, a linear aldehyde—such as that formed in the hydroformylation step—can be contacted with any catalyst composition disclosed herein (e.g., transition metal compound, phosphine, heteroatomic acid or derivative, and acceptor) to form a second normal alpha olefin having the structure $CH_3(CH_2)_{2n+1}HC=CH_2$. In this process, n can be an integer ranging from 0 to 15; for example, n can be an integer from 0 to 10, n can be an integer from 0 to 7, n can be an integer from 1 to 7, or n can be an integer from 1 to 5. Accordingly, in some aspects, the second normal alpha olefin can comprise (or consist essentially of, or consist of) ethylene, propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof; alternatively, 1-butene, 1-hexene, 1-octene, 1-decene, 1-dodecene, or any combination thereof; alternatively, 1-hexene, 1-octene, 1-decene, 1-dodecene, 1-tetradecene, or any combination thereof; or alternatively, 1-hexene, 1-octene, 1-decene, or any combination thereof. In other aspects, the second normal alpha olefin can comprise (or consist essentially of, or consist of) 1-hexene; alternatively, 1-octene; or alternatively, 1-decene.

Step (iii) of the sixth process can be performed in the same manner as that described above for the first process, second process, and third process. Thus, any acceptor disclosed herein can be used, and the molar ratio of the acceptor to the linear aldehyde can be any amount in the range from about 0.2:1 to about 1000:1. Likewise, the molar ratio of the linear aldehyde to the transition metal of the transition metal compound or the phosphine transition metal compound complex (in the catalyst composition) can be any molar ratio in the range from about 2:1 to about 1000:1. Further, step (iii) can be performed in any solvent disclosed in relation to the first process, the second process, and the third process (e.g., toluene, THF, dioxane) and at any temperature (e.g., from about 0° C. to about 150° C.), pressure, WHSV or reaction time, and further, the second normal alpha olefin product can be isolated or separated from reaction by-products, residual reactants, catalyst systems components, and the like, using any suitable technique.

Generally, the yield of the second normal alpha olefin (moles of second normal alpha olefin based on the moles of the linear aldehyde) in step (iii) of this multistep process can be at least about 10%, at least about 20%, at least about 30%, at least about 40%, or at least about 50%. In certain aspects, the presence of an acceptor in the catalyst composition can unexpectedly and drastically improve the yield of the second normal alpha olefin, while minimizing byproducts such as internal olefins. In such circumstances, the molar yield can be at least about 60%, at least about 70%, at least about 80%, at least about 90%, at least about 95%, at least about 98%, or at least about 99%. The amount of by-products, such as alkanes and internal olefins, formed in step (iii) of the multistep process can be less than about 20%, less than about 15%, less than about 10%, less than about 8%, less than about 5%, less than about 3%, less than about 2%, or less than about 1%. These percentages are molar yields based on the initial amount of the linear aldehyde).

In another aspect of this invention, a seventh process for producing a normal alpha olefin is provided, and in this aspect, the process can comprise (or consist essentially of, or consist of) (a) contacting a linear internal olefin having the structure $CH_3(CH_2)_pHC=CH(CH_2)_qCH_3$ with a hydroformylation catalyst system, carbon monoxide, and hydrogen to form a linear aldehyde having the formula $CH_3(CH_2)_{p+q+3}C(=O)H$, and (b) contacting the linear aldehyde with any catalyst composition disclosed herein (e.g., transition metal compound, phosphine, heteroatomic acid or derivative, and acceptor) to form a normal alpha olefin having the structure $CH_3(CH_2)_{p+q+1}HC=CH_2$. In the seventh process, p and q can be integers that independently can range from 0 to 15. In this process, p and q can be the same or different; alternatively, the same; or alternatively, different. Generally, the features of the seventh process (e.g., the linear internal olefin, the hydroformylation catalyst system, the linear aldehyde, the catalyst composition, the normal alpha olefin, and the conditions under which each of the steps are conducted, among other features) are independently described herein and these features can be combined in any combination to further describe the seventh normal alpha olefin synthesis process. Moreover, additional process steps can be performed before, during, and/or after any of the steps of any of the processes disclosed herein, unless stated otherwise.

For instance, the internal olefin having the formula $CH_3(CH_2)_pHC=CH(CH_2)_qCH_3$ can be produced by any method known to those having ordinary skill in the art. In an aspect, the linear internal olefin having the structure $CH_3(CH_2)_pHC=CH(CH_2)_qCH_3$ can be produced by the metathesis of an alpha olefin having the formula $CH_3(CH_2)_pHC=CH_2$ and an alpha olefin having the formula $CH_3(CH_2)_qHC=CH_2$: e.g., the process for producing a normal alpha olefin can further comprise a step of contacting a normal alpha olefin having the structure $CH_3(CH_2)_pHC=CH_2$, a normal alpha olefin having the formula $CH_3(CH_2)_qHC=CH_2$, and a metathesis catalyst system to form the linear internal olefin having the structure $CH_3(CH_2)_pHC=CH(CH_2)_qCH_3$. In another aspect, the linear internal olefin having the structure $CH_3(CH_2)_pHC=CH(CH_2)_qCH_3$ can be produced by the dehydrogenation of a linear alkane having the formula $CH_3(CH_2)_{p+q+2}CH_3$.

In the seventh process, step (a) is often referred to as the hydroformylation step, and step (a) can have any of the features and attributes (e.g., the hydroformylation catalyst system) as that described herein for hydroformylation step (ii) in the sixth process. Likewise, step (b) of the seventh process is often referred to as the dehydroformylation step, and step (b) can have any of the feature or attributes as that described herein for the first process, the second process, and the third process: the acceptor, the catalyst composition, the molar ratio of the acceptor to the linear aldehyde, the molar ratio of the linear aldehyde to the transition metal, the solvent, the reaction temperature, the reaction pressure, the WHSV or reaction time, and the yield of the normal alpha olefin (moles of normal alpha olefin based on the moles of the linear aldehyde), among others.

In this normal alpha olefin synthesis process, p and q independently can be integers that range from 0 to 15. In one aspect consistent with this invention, p and q independently can be an integer from 0 to 10, while in another aspect, p and q independently can be an integer from 0 to 7. Yet, in another aspect, p and q independently can be an integer from 1 to 7, and in still another aspect, p and q independently can be an integer from 1 to 5. For example, p and q independently can be equal to 1, equal to 2, equal to 3, or equal to 4.

The normal alpha olefin produced in this process, having the structure $CH_3(CH_2)_{p+q+1}HC=CH_2$, is not particularly limited. However, in one aspect of this invention, the normal alpha olefin can comprise, consist essentially of, or consist of, ethylene, propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof; alternatively, 1-butene, 1-hexene, 1-octene, 1-decene, 1-dodecene, or any combination thereof; alternatively, 1-butene, 1-hexene, 1-octene, 1-decene, 1-dodecene, 1-tetradecene, 1-hexadecene, 1-octadecene, or any combination thereof; alternatively, 1-hexene, 1-octene, 1-decene, 1-dodecene, 1-tetradecene, or any combination thereof; or alternatively, 1-hexene, 1-octene, 1-decene, or any combination thereof. In another aspect, the normal alpha olefin can comprise, consist essentially of, or consist of, 1-butene; alternatively, 1-hexene; alternatively, 1-octene; alternatively, 1-decene; alternatively, 1-dodecene; alternatively, 1-tetradecene; alternatively, 1-hexadecene; or alternatively, 1-octadecene. In yet another aspect, the normal alpha olefin can comprise, consist essentially of, or consist of, 1-hexene, 1-octene, 1-decene, or any combination thereof.

The integer p, the integer q, and the normal alpha olefin are described herein and their features can be utilized without limitation to further describe the seventh normal alpha olefin synthesis process disclosed herein. Other suitable values for the integer p and the integer q, and selections for the normal alpha olefin, are readily apparent from this disclosure.

In an aspect, wherein the linear internal olefin is produced via metathesis, 1) the normal alpha olefin having the structure $CH_3(CH_2)_pHC{=}CH_2$ can be propene, 2) the normal alpha olefin having the formula $CH_3(CH_2)_qHC{=}CH_2$ can be pentene, 3) the linear internal olefin can be a linear internal butene, a linear internal hexene, a linear internal octene, or any combination thereof, and 4) the normal alpha olefin having the structure $CH_3(CH_2)_{p+q+1}HC{=}CH_2$ can be 1-butene, 1-hexene, 1-octene, or any combination thereof, or alternatively, 1) the normal alpha olefin having the structure $CH_3(CH_2)_pHC{=}CH_2$ can be propene, 2) the normal alpha olefin having the formula $CH_3(CH_2)_qHC{=}CH_2$ can be heptene, 3) the linear internal olefin can be a linear internal butene, a linear internal octene, a linear internal dodecene, or any combination thereof, and 4) the normal alpha olefin having the structure $CH_3(CH_2)_{p+q+1}HC{=}CH_2$ can be 1-butene, 1-octene, 1-dodecene, or any combination thereof. In some aspects, wherein the linear internal olefin is produce via metathesis, 1) the normal alpha olefin having the structure $CH_3(CH_2)_pHC{=}CH_2$ can be butene, 2) the normal alpha olefin having the formula $CH_3(CH_2)_qHC{=}CH_2$ can be hexene, 3) the linear internal olefin can be a linear internal hexene, a linear internal octene, a linear internal decene, or any combination thereof, and 4) the normal alpha olefin having the structure $CH_3(CH_2)_{p+q+1}HC{=}CH_2$ can be 1-hexene, 1-octene, 1-decene, or any combination thereof; or alternatively, 1) the normal alpha olefin having the structure $CH_3(CH_2)_pHC{=}CH_2$ can be butene, 2) the normal alpha olefin having the formula $CH_3(CH_2)_qHC{=}CH_2$ can be octene, 3) the linear internal olefin can be a linear internal hexene, a linear internal decene, a linear internal tetradecene, or any combination thereof, and 4) the normal alpha olefin having the structure $CH_3(CH_2)_{p+q+1}HC{=}CH_2$ can be 1-hexene, 1-decene, 1-tetradecene, or any combination thereof. In other aspects, wherein the linear internal olefin is produce via metathesis, 1) the normal alpha olefin having the structure $CH_3(CH_2)_pHC{=}CH_2$ can be pentene, 2) the normal alpha olefin having the formula $CH_3(CH_2)_qHC{=}CH_2$ can be heptene, 3) the linear internal olefin can be a linear internal octene, a linear internal decene, a linear internal dodecene, or any combination thereof, and 4) the normal alpha olefin having the structure $CH_3(CH_2)_{p+q+1}HC{=}CH_2$ can be 1-octene, 1-decene, 1-dodecene, or any combination thereof. Other combinations of 1) a normal alpha olefin having the structure $CH_3(CH_2)_pHC{=}CH_2$, 2) a normal alpha olefin having the formula $CH_3(CH_2)_qHC{=}CH_2$, 3) a linear internal olefin, and 4) a normal alpha olefin having the structure $CH_3(CH_2)_{p+q+1}HC{=}CH_2$ are readily apparent from this disclosure.

EXAMPLES

The invention is further illustrated by the following examples, which are not to be construed in any way as imposing limitations to the scope of this invention. Various other aspects, modifications, and equivalents thereof which, after reading the description herein, can suggest themselves to one of ordinary skill in the art without departing from the spirit of the present invention or the scope of the appended claims.

Example 1

Reaction of 1-Dodecanol Without an Acceptor

Example 1 was conducted by combining 1-dodecanol (0.2 mmol), [Rh(cod)OMe]$_2$ (2 mol %), 3-OMeBzOH (4 mol %), and Xantphos (4 mol %) in 0.4 mL toluene and heating the solution to 90° C. (see reaction scheme below). The reaction continued for 24 h before analyzing the crude reaction mixture by gas chromatography using durene as an internal standard to determine the amount of 1-undecene, 1-undecane, and undecene isomers present in the reaction mixture. Gas chromatography analysis determined that only 1-undecane was present in the reaction mixture (10 mol % yield).

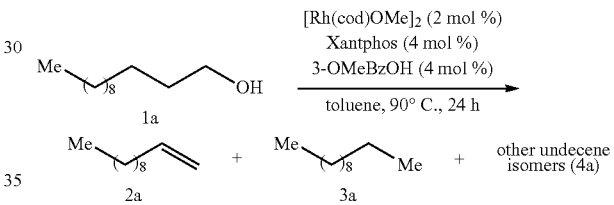

Examples 1A-1K

Reaction of 1-Dodecanol in the Presence of Various Acceptors

Examples 1A-1K utilized the general experimental procedure described above for Example 1, except that an acceptor (3 molar equivalents based on the primary alcohol) was used. Examples 1A-1K were conducted as single, individual experiments; results from each reaction are shown in Table 1 below. Surprisingly, Example 1K, which employed dimethylacrylamide as the acceptor, exhibited a dramatic and unexpected improvement to the selectivity of the reaction with respect to the $C_{(n-)}$ olefin product, producing a 95% molar yield of the desired 1-undecene product, and only about 3 mol % of alkane and internal olefin byproducts. Moreover, Examples 1H-1J also demonstrated excellent selectivity, each having a yield of 1-undecene above 30%, using ethyl acrylate, t-butyl acrylate, and acrylamide, respectively.

TABLE 1

| Example | Acceptor | 1-undecene | 1-undecane | Isomers |
|---|---|---|---|---|
| 1A | ⬡ | 32 | — | 2 |

TABLE 1-continued

| Example | Acceptor | 1-undecene | 1-undecane | Isomers |
|---------|----------|------------|------------|---------|
| 1B | norbornene | 18 | — | 8 |
| 1C | acetone | — | 15 | — |
| 1D | cyclopentanone | — | 30 | — |
| 1E | PhC(O)CF₃ | — | 12 | — |
| 1F | methyl vinyl ketone | 10 | 7 | 2 |
| 1G | acrylonitrile | 3 | 9 | — |
| 1H | ethyl acrylate | 33 | 1 | 1 |
| 1I | t-butyl acrylate | 41 | 2 | 1 |
| 1J | acrylamide | 35 | 2 | 1 |
| 1K | dimethylacrylamide | 95 | 1 | 2 |

Examples 2A-2T

Reaction of Various Primary Alcohol Compounds Using Dimethylacrylamide as the Acceptor Examples 2A-2T utilized the general experimental procedure described above for Inventive Example 1K (dimethylacrylamide), except that the primary alcohol compound reactant was substituted as indicated in the chart below; and except that 2H used 6 molar equivalents of dimethylacrylamide to account for the dual primary alcohol groups present in the starting material. The compounds shown below represent the primary alcohol compound and olefin product superimposed over the same structure; the dashed bonds represent the carbon-carbon bond broken during the reaction. Surprisingly, the oxidative dehydroxymethylation processes demonstrated a molar yield of the expected olefin in a range from 75% to 95%. Thus, the reaction is shown to be incredibly robust across compounds having protected groups (2L-2T) or additional functional groups comprising a π-bond present in the compound (2B-2G).

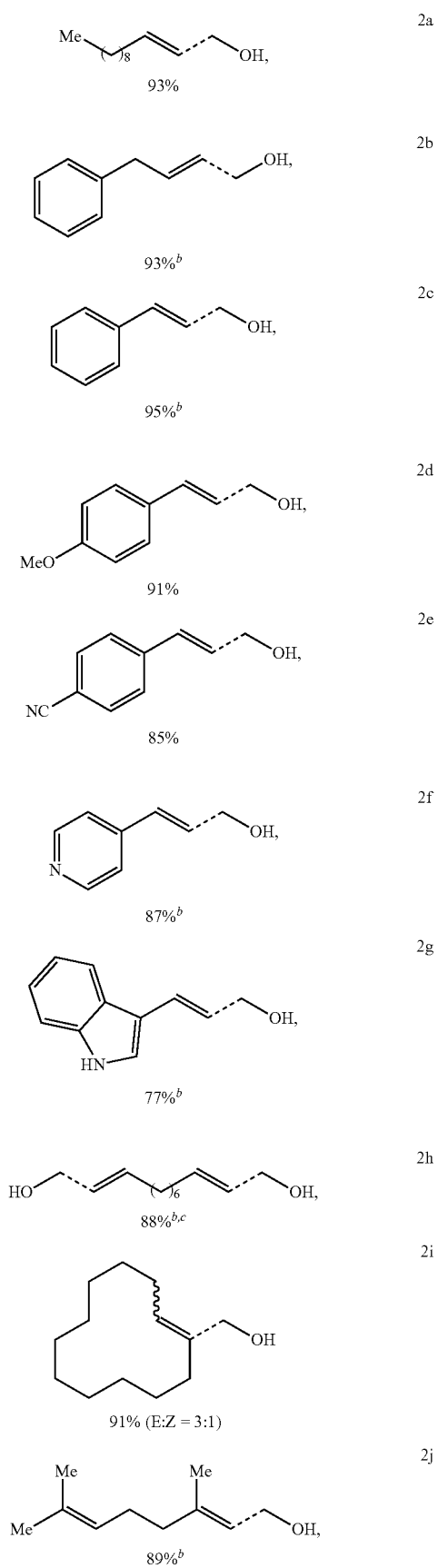

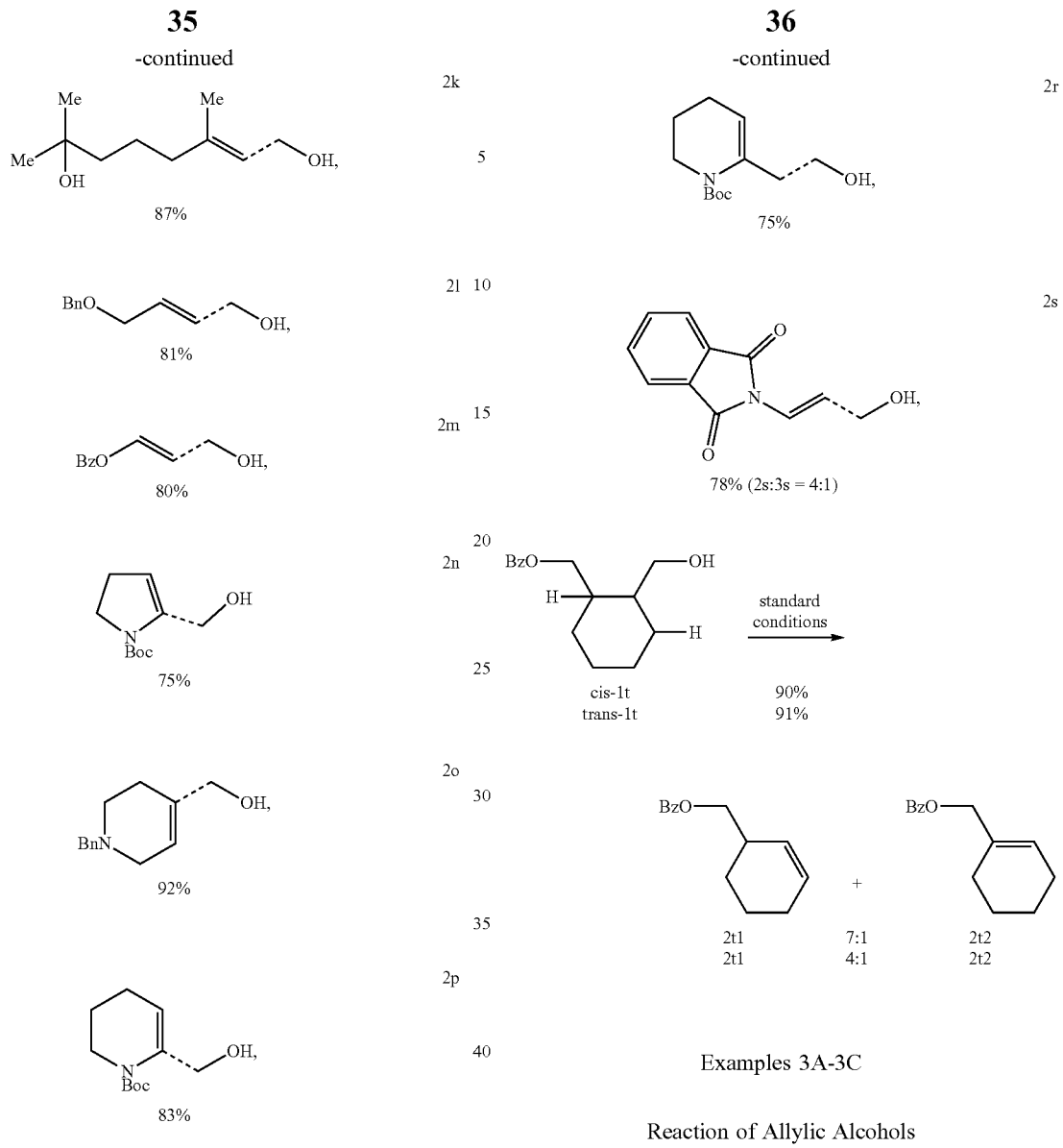

Examples 3A-3C

Reaction of Allylic Alcohols

Examples 3A-3C utilized the general experimental procedure described above for Inventive Example 1K (dimethylacrylamide), except that the primary alcohol compound reactant was substituted as indicated in the scheme below and only 1.5 equivalents of dimethylacrylamide were used. Surprisingly, the terminal olefin was produced in high yield, and without significant byproducts.

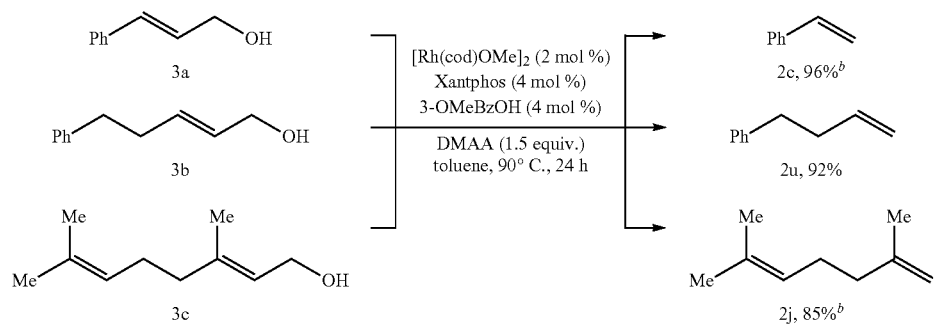

Example 4

Oxidative Dehydroformylation of an Aldehyde Compound

Example 4 utilized the general experimental procedure described above for Inventive Examples 3A-3C, except that the primary alcohol compound reactant was substituted for aldehyde compound 4, and the amount of [Rh(cod)OMe]$_2$ (0.5 mol %), 3-OMeBzOH (1 mol %), and Xantphos (1 mol %) were reduced, and the reaction time was only 3 h. Surprisingly, the α-olefin product was formed in 94% yield in only 3 h, even though a comparatively small amount of the catalyst composition was used in the reaction.

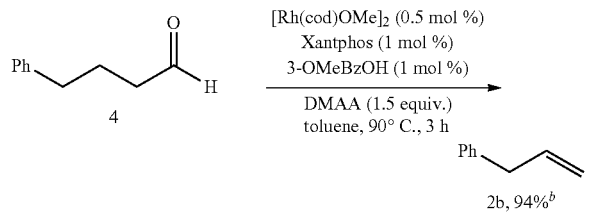

Examples 5A-5B

Dehomologations of Olefin Feedstocks

Examples 5A-5B represent a synthetic pathway to one-carbon and two-carbon dehomologations of a common olefin feedstock, 1-dodecene (reaction schemes below).

In Example 5A, 1-dodecene was subjected to a two-step synthesis including (i) hydroboration-oxidation of 1-dodecene by established methods to yield 1-dodecanol, and (ii) oxidative dehydroxymethylation of 1-dodecanol according to the general experimental procedure described above for Inventive Example 1K. The two-step process yielded the C$_{11}$ α-olefin in excellent yield (86%).

In Example 5B, 1-dodecene was subjected to a two-step process including (i) olefin dihydroxylation of 1-dodecene by established methods to yield 1,2-dodecanediol, and (ii) successive oxidative dehydroxymethylations of 1,2-dodecanediol according to the general experimental procedure described above for Inventive Example 1K, using twice the amount of sacrificial acceptor (4 molar equivalents) to account for the removal of an additional hydroxyl group (as in Example 2H). The two-step process yielded the C$_{10}$ α-olefin in good yield (75%).

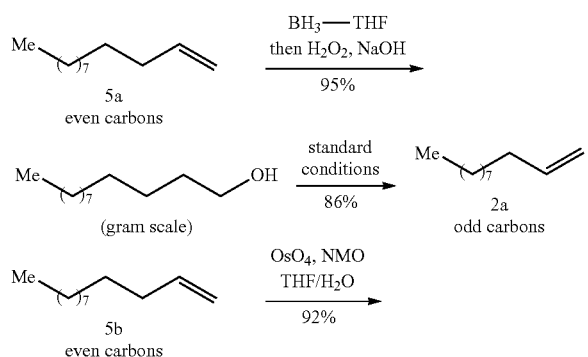

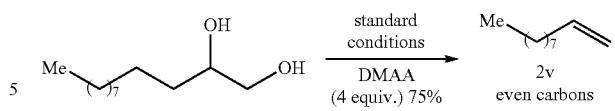

Examples 6A-6C

Natural Product Synthesis

Examples 6A-6C demonstrate the utility of the oxidative dehydroxymethylation processes disclosed herein for the synthesis of complex structures and in the presence of benzyl protecting groups or secondary hydroxyl groups. Each of Examples 6A-6C underwent oxidative dehydroxymethylation according to the general experimental procedure described above for Inventive Example 1K.

Example 6A provides an example of oxidative dehydroxymethylation performed in the presence of protected alcohol groups. Surprisingly, no debenzylation was observed, and the α-olefin product was formed in good yield.

Example 6B demonstrates oxidative dehydroxymethylation of a compound containing two unprotected secondary alcohol functional groups: one sterically accessible and one sterically hindered. Surprisingly, the sterically hindered secondary hydroxyl group was unaffected by the reaction. Further, the sterically accessible secondary hydroxyl group was converted to a ketone, and no further conversion of the ketone to an alkene was observed.

Example 6C takes advantage of the chemoselectivity demonstrated in Example 6B to provide a synthetic route to (+)-yohimbenone from yohimbenol in a single step. As shown below, the primary alcohol is converted to a Michael acceptor in good yield, despite the product being available as a potential sacrificial acceptor as the reaction progresses.

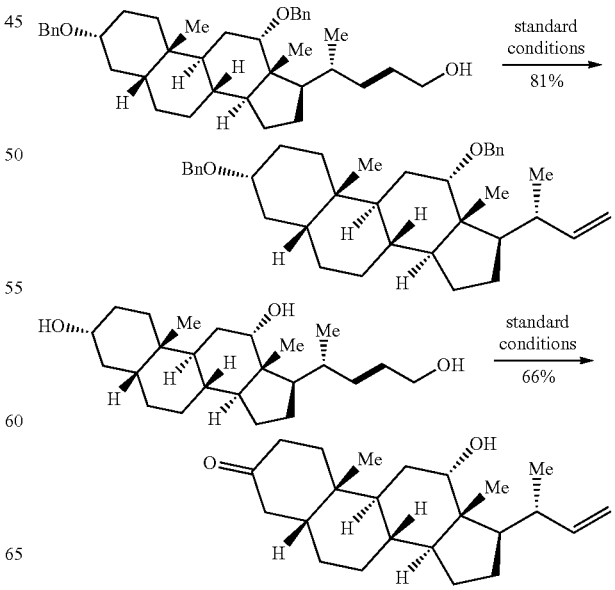

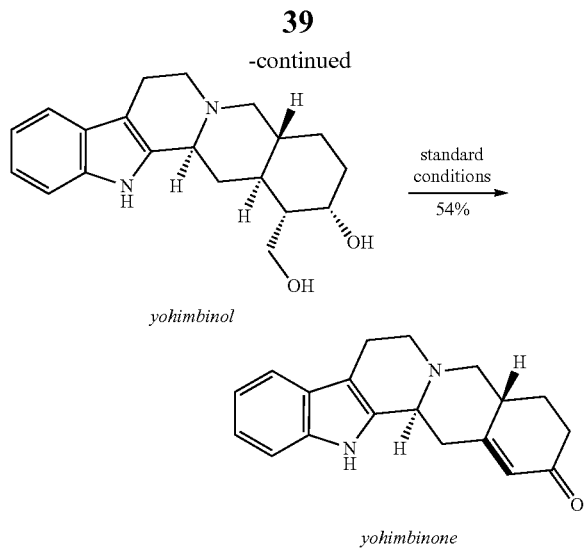

*yohimbinol*

*yohimbinone*

Constructive Example 7

Constructive Example 7 demonstrates the conversion of 1-hexene to 1-decene via a metathesis (homogeneous), isomerization-hydroformylation (un-ligated), and dehydroformylation pathway as shown in the synthesis scheme below (where n=3).

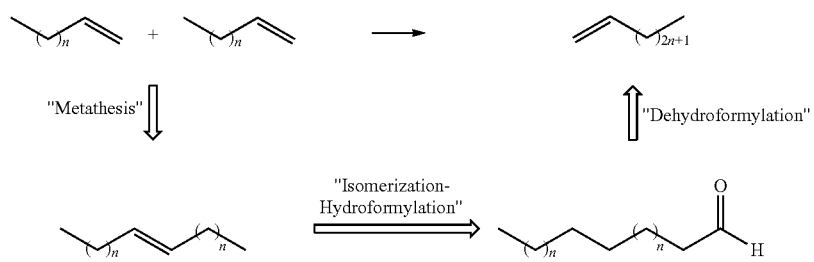

The reaction scheme for the homogeneous metathesis step is shown below.

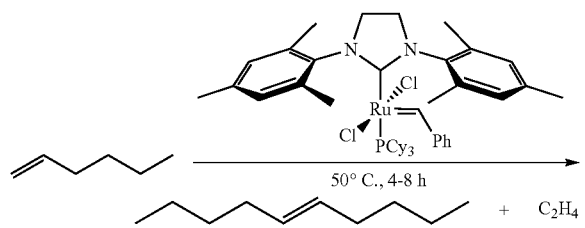

The metathesis step can be performed as follows. In a drybox under an $N_2$ atmosphere, a 500 mL round bottom flask with a magnetic stir bar is charged with 1-hexene (250 mL, 168 g, ~2 mol). The flask is placed in an aluminum block on a temperature controlled heating plate at ~50° C. and allowed to equilibrate temperature. To this stirring solution, a Grubbs $2^{nd}$ Generation Catalyst (dichloro [1,3-bis(2,4,6-trimethylphenyl)-2-imidazolidinylidene] (benzylidene) (tricyclohexylphosphine) ruthenium(II), 4.2 mg, 4.9 μmol) is added to initiate the reaction. Reaction progress can be monitored by taking aliquot samples and analyzing them by GC-FID for reaction equilibrium, which typically takes 4-8 hr. Any produced ethylene is allowed to bubble and leave the flask as it is not capped in the glovebox. Upon completion of the reaction, the solution is cooled, filtered, and the reaction contents distilled to isolate 5-decene. The reaction yield is ~40-50% 5-decene by fractional distillation.

The reaction scheme for the isomerization-hydroformylation (un-ligated) step is shown below.

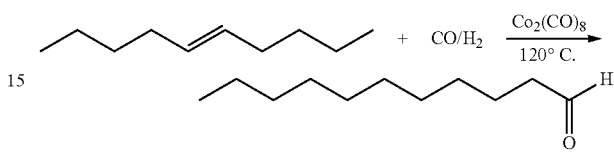

The isomerization-hydroformylation step can be performed as follows. A 5 L continuously stirred autoclave is charged with 190 g (1 mol) of 5-decene in 3.8 L of benzene and 4.27 g (0.0125 mol) of recently sublimed $Co_2(CO)_8$. The decene:cobalt molar ratio is maintained at ~40:1. The autoclave is pressurized with 3000 psig of a 1:1 mix of Syn-Gas mixture ($CO:H_2$) that is fed on demand and is heated at 120° C. until the reaction reaches 40-60% conversion, as monitored by aliquot sampling and GC-FID analysis. GC-FID reveals that, upon analysis of the reaction, greater than 50% of the internal olefin is converted to the primary aldehyde, 1-undecanal. The remainder of the product is a mixture of the various internal aldehydes declining in yield from the primary position. The products then can be individually isolated by fractional distillation to yield 90+% pure 1-undecanal.

The reaction scheme for the dehydroformylation step is shown below.

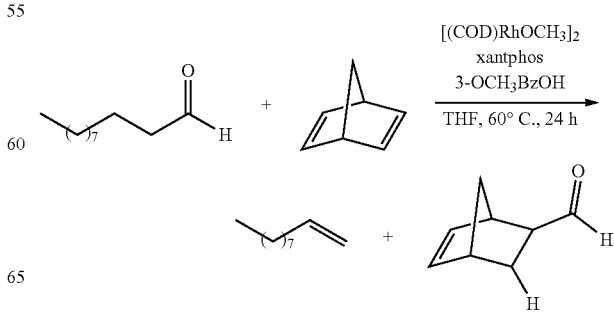

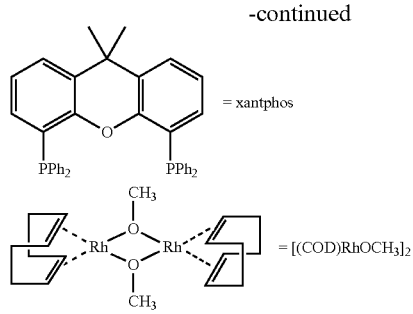

The dehydroformylation step to produce 1-decene can be performed as follows. In a drybox under an $N_2$ atmosphere, a 500 mL round bottom flask with a magnetic stir bar is charged with $[(COD)RhOCH_3]_2$ (2.72 g, 5 mmol), xantphos (5.79 g, 10 mmol), 3-methoxybenzoate (1.52 g, 10 mmol), 1-undecanal (170 g, 1 mol), and 250 mL (~3 mol) of THF. Norbornadiene (111 g, 1.2 mol) is then added last to the reaction mixture. The flask is placed in an aluminum block on a temperature controlled heating plate for 24 hr at 60° C. Reaction progress is monitored by taking aliquot samples and analyzing via GC-FID. Upon completion of the reaction, the reaction mixture is cooled, filtered, and the reaction product is distilled to isolate decene by fractional distillation. Product yield is 90+% decenes in a 95:5 ratio of 1-decene:2-decene, as determined by GC-FID.

Constructive Example 8

Constructive Example 8 demonstrates the conversion of 1-hexene to 1-decene via a metathesis (heterogeneous), isomerization-hydroformylation (ligated), and dehydroformylation pathway as shown in the synthesis scheme below (where n=3).

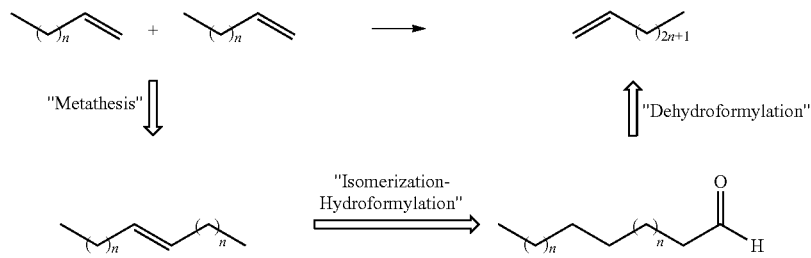

The reaction scheme for the heterogeneous metathesis step is shown below.

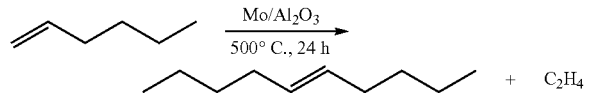

The metathesis step can be performed as follows. A 4-inch I.D. by 5-foot long stainless steel pipe is heated electrically for controlling reactor temperature and for catalyst activation/regeneration. The reactor contains 8.2 kg of molybdenum oxide-on-alumina catalyst (1.3% $MoO_3$, 0.07% $SiO_2$) from Nalco Chemical Company, consisting of ⅛" extrudate pellets treated with 1.5 wt. % KOH. The catalyst is regenerated by "burning off" polymer and hydrocarbons, and holding the catalyst for 6 hr at 565° C. under air. The catalyst temperature is then reduced and the atmosphere changed to $N_2$. 1-hexene is distilled prior to use and charged to an olefin feed vessel. From the feed vessel, the 1-hexene is pumped at constant rate upflow through the catalyst bed. Reaction conditions are typically 87-110° C., at 20 psig pressure, with an LHSV of 0.5. The product then can be flowed into a product hold vessel, where ethylene is allowed to be flashed overhead. The crude product is then sent to a kettle bottom of a distillation column and distilled until the concentration of 5-decene in the kettle bottom reaches ~80%. At this point, approximately, 20 L of crude kettle product is obtained. The crude kettle product, approximately 73 kg, is loaded into the kettle of a 2" stainless steel distillation column with ¼" Octapac and distilled with 5-decene coming as the last cut at 86-89° C. at 50 mm Hg to yield approximately 41 kg of 5-decene with the following estimated specifications:

| | |
|---|---|
| Purity (wt. %) | 99.6 |
| cis 5-decene (wt. %) | 18.1 |
| trans 5-decene (wt. %) | 81.5 |
| Specific gravity (20/20° C.) | 0.742 |
| Refractive index ($N_D^{20}$) | 1.428 |
| Freezing point (° C.) | −75.8 |
| Boiling point (° C.) | 169.8 |

The reaction scheme for the isomerization-hydroformylation (ligated) step is shown below.

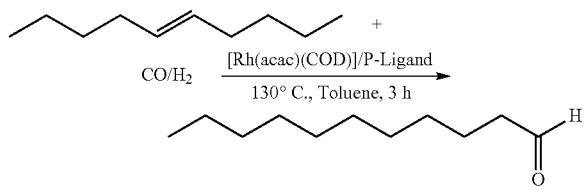

-continued

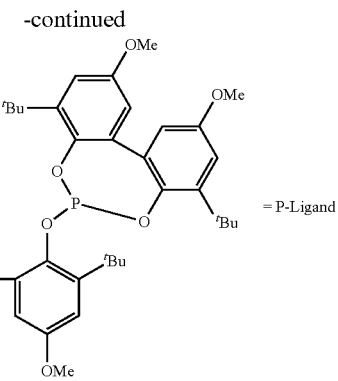

The isomerization-hydroformylation step can be performed as follows. A 1 L continuously stirred autoclave is charged with 600 mL of a 1.68 M solution of 5-decene (~190 g, 1 mol) in toluene, 0.2 g (0.63 mmol) of [Rh(acac)(COD)], and 5.8 g (6.4 mmol) of 3-aryloxy-1,3,2-dioxaphosphine-4-ones ligand, P-Ligand. The autoclave is pressurized with 300 psig of a 1:1 mix of syngas mixture (CO:H$_2$) that is fed on demand and is heated at 130° C. for 3 hr. GC-FID reveals that, upon analysis of the reaction, greater than 65% of the internal olefin is converted to the primary aldehyde, 1-undecanal. The remainder of the product is a mixture of the various internal aldehydes declining in yield from the primary position. The products then can be individually isolated by fractional distillation to yield 90+% pure 1-undecanal.

The reaction scheme for the dehydroformylation step is shown below.

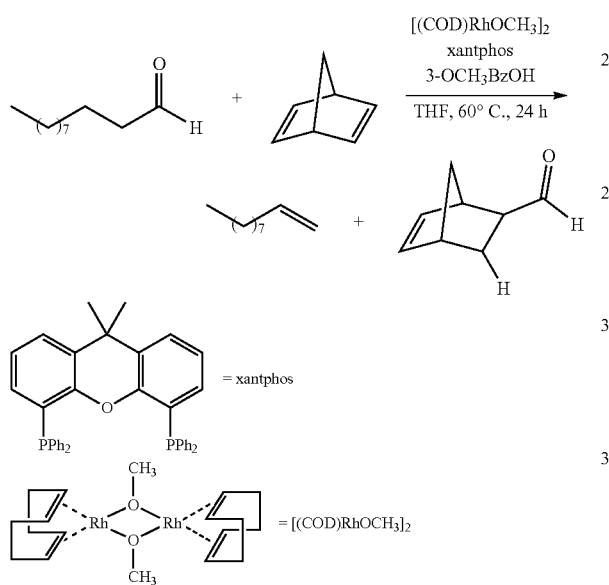

The dehydroformylation step to produce 1-decene can be performed as follows. In a drybox under an N$_2$ atmosphere, a 500 mL round bottom flask with a magnetic stir bar is charged with [(COD)RhOCH$_3$]$_2$ (2.72 g, 5 mmol), xantphos (5.79 g, 10 mmol), 3-methoxybenzoate (1.52 g, 10 mmol), 1-undecanal (170 g, 1 mol), and 250 mL (~3 mol) of THF. Norbornadiene (111 g, 1.2 mol) is then added last to the reaction mixture. The flask is placed in an aluminum block on a temperature controlled heating plate for 24 hr at 60° C. Reaction progress is monitored by taking aliquot samples and analyzing via GC-FID. Upon completion of the reaction, the reaction mixture is cooled, filtered, and the reaction product is distilled to isolate decene by fractional distillation. Product yield is 90+% decenes in a 95:5 ratio of 1-decene:2-decene, as determined by GC-FID.

The invention is described herein with reference to numerous aspects and specific examples. Many variations will suggest themselves to those skilled in the art in light of the detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A catalyst composition comprising:
(I) a transition metal compound, a phosphine, and a heteroatomic acid or heteroatomic acid derivative, or (II) a phosphine transition metal compound complex and a heteroatomic acid or heteroatomic acid derivative.

Aspect 2. The composition defined in aspect 1, wherein the transition metal compound or the transition metal compound of the phosphine transition metal compound complex comprises a rhodium compound.

Aspect 3. The composition defined in aspect 1, wherein the transition metal compound or the transition metal compound of the phosphine transition metal compound complex comprises an olefin rhodium alkoxide complex.

Aspect 4. The composition defined in aspect 1, wherein the transition metal compound or the transition metal compound of the phosphine transition metal compound complex comprises a cyclodiene rhodium alkoxide complex.

Aspect 5. The composition defined in any one of aspects 1-4, wherein the phosphine or the phosphine of the phosphine transition metal compound complex comprises any suitable alkyl phosphine and/or aryl phosphine.

Aspect 6. The composition defined in any one of aspects 1-4, wherein the phosphine or the phosphine of the phosphine transition metal compound complex is a diphosphine having structure (I):

wherein:
L$^1$ is a linking group; and
each R independently is H or a C$_1$ to C$_{18}$ hydrocarbyl group, a C$_1$ to C$_{18}$ hydrocarboxy group, or a C$_1$ to C$_{18}$ hydrocarbylaminyl group.

Aspect 7. The composition defined in any one of aspects 1-4, wherein the phosphine or the phosphine of the phosphine transition metal compound complex is a diphosphine comprising a 1,6-bisphosphinylhexane, a substituted 1,6-bisphosphinylhexane, a (1,3-phenylenedi-1,1-ethanediyl)bis(phosphine), a substituted (1,3-phenylenedi-1,1-ethanediyl-bis(phosphine), a 1,8-anthracenediylbis(phosphine), a substituted 1,8-anthracenediylbis(phosphine), a 1,8-tetradecahydroanthracenediylbis(phosphine), or a substituted 1,8-tetradecahydroanthracenediylbis(phosphine), a (methylenedi-2,1-phenylene)bis(phosphine), a substituted (methylenedi-2,1-phenylene)bis(phosphine), a 9H-xanthene-4,5-diylbis(phosphine), a substituted 9H-xanthene-4,5-diylbis(phosphine), or a combination thereof.

Aspect 8. The composition defined in any one of aspects 1-4, wherein the phosphine or the phosphine of the phosphine transition metal compound complex is a diphosphine having any one of the following structures:

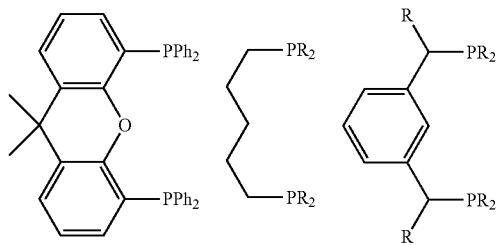

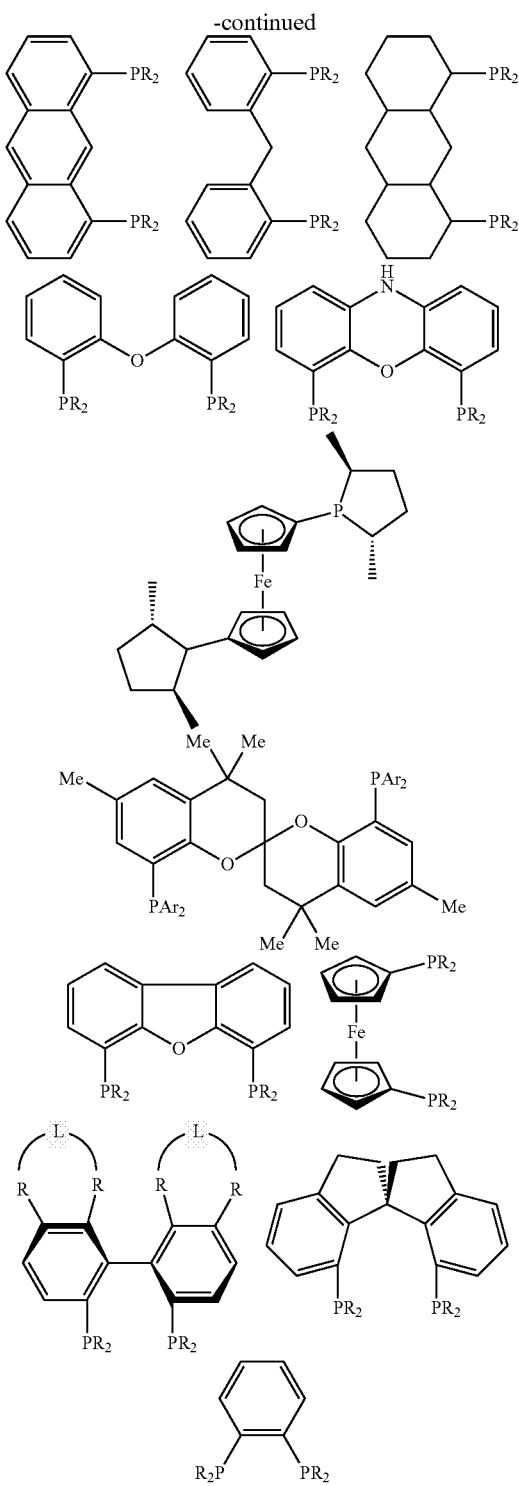

wherein:
Ph is a phenyl group;
Me is a methyl group;
Ar is an aromatic group;
each R independently is H or a $C_1$ to $C_{18}$ hydrocarbyl group, a $C_1$ to $C_{18}$ hydrocarboxy group, or a $C_1$ to $C_{18}$ hydrocarbylaminyl group; and
L is a linking group.

Aspect 9. The composition defined in any one of aspects 1-8, wherein the heteroatomic acid or heteroatomic acid derivative comprises a carboxylic acid, an alcohol, a mineral acid, an ammonium salt, an amine, a thiol, etc., or any combination thereof.

Aspect 10. The composition defined in any one of aspects 1-8, wherein the heteroatomic acid or heteroatomic acid derivative comprises benzoic acid or a substituted benzoic acid, or a salt or ester of benzoic acid or a substituted benzoic acid.

Aspect 11. The composition defined in any one of the preceding aspects, wherein the molar ratio of the transition metal of the transition metal compound to the phosphine (or diphosphine) is in a range from about 0.2:1 to about 5:1 (or have any other minimum value, maximum value, or range described herein).

Aspect 12. The composition defined in any one of the preceding aspects, wherein the molar ratio of the transition metal of the transition metal compound or the phosphine transition metal compound complex to the heteroatomic acid or heteroatomic acid derivative is in a range from about 0.8:1 to about 5:1 (or have any other minimum value, maximum value, or range described herein).

Aspect 13. The composition defined in any one of the preceding aspects, wherein the catalyst composition further comprises an acceptor.

Aspect 14. The composition defined in aspect 13, wherein the acceptor (e.g., acceptor olefin) comprises a mono-olefin compound (e.g., ethylene, norbornene), a di-olefin compound (e.g., cyclooctadiene, norbornadiene), a tri-olefin compound (e.g., cyclododecatriene), or any combination thereof.

Aspect 15. The composition defined in aspect 13 or 14, wherein the acceptor (e.g., acceptor olefin) is an aliphatic hydrocarbon compound.

Aspect 16. The composition defined in aspect 13 or 14, wherein the acceptor (e.g., acceptor olefin) is a heteroatomic olefin compound, e.g., an enone, an enamine, an enol, an enamide (acrylamide), etc., or any combination thereof.

Aspect 17. The composition defined in any one of aspects 13-16, wherein the acceptor (e.g., acceptor olefin) is a cyclic compound.

Aspect 18. The composition defined in aspect 13, wherein the acceptor comprises an unsaturated triglyceride or an unsaturated natural source oil, e.g., soybean oil, corn oil, castor bean oil, canola oil, or any combination thereof.

Aspect 19. The composition defined in aspect 13, wherein the acceptor comprises an aliphatic mono-olefin hydrocarbon, an aliphatic di-olefin hydrocarbon, an aliphatic tri-olefin hydrocarbon, or any combination thereof.

Aspect 20. A dehydroxymethylation process comprising: contacting a saturated linear $C_3$-$C_{36}$ hydrocarbon primary alcohol with the catalyst composition defined in any one of aspects 1-19 to form a $C_2$-$C_{35}$ normal alpha olefin.

Aspect 21. A dehydroxymethylation process comprising: contacting a saturated linear $C_4$-$C_{36}$ hydrocarbon terminal vicinal diol with the catalyst composition defined in any one of aspects 1-19 to form a $C_2$-$C_{34}$ normal alpha olefin.

Aspect 22. A dehydroformylation process comprising: contacting a saturated linear $C_3$-$C_{36}$ hydrocarbon aldehyde with the catalyst composition defined in any one of aspects 1-19 to form a $C_2$-$C_{35}$ normal alpha olefin.

Aspect 23. The process defined in any one of aspects 20-22, wherein the step of contacting is performed in a solvent (e.g., toluene, THF, dioxane).

Aspect 24. The process defined in any one of aspects 20-23, wherein the step of contacting is performed at a temperature from about 0° C. to about 150° C. (or any other minimum temperature, maximum temperature, or temperature range described herein).

Aspect 25. The process defined in any one of aspects 20-24, wherein a molar ratio of the acceptor to the primary alcohol (or vicinal diol, or linear aldehyde) is in a range from about 0.2:1 to about 1000:1, or from about 0.5:1 to about 5:1 (or have any other minimum value, maximum value, or range described herein).

Aspect 26. The process defined in any one of aspects 20-25, wherein a molar ratio of the primary alcohol (or vicinal diol, or linear aldehyde) to the transition metal of the transition metal compound or the phosphine transition metal compound complex is in a range from about 2:1 to about 1000:1, or from about 10:1 to about 250:1 (or have any other minimum value, maximum value, or range described herein).

Aspect 27. The process defined in any one of aspects 20-26, wherein a molar yield of the normal alpha olefin is at least about 20%, at least about 50%, at least about 75%, or at least about 90%, based on the primary alcohol (or vicinal diol, or linear aldehyde) (or have any other value, or range described herein).

Aspect 28. The process defined in any one of aspects 20-27, wherein the normal alpha olefin comprises a $C_4$-$C_{16}$ normal alpha olefin.

Aspect 29. The process defined in any one of aspects 20-27, wherein the normal alpha olefin comprises ethylene, propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof.

Aspect 30. The process defined in any one of aspects 20-27, wherein the normal alpha olefin comprises 1-butene, 1-hexene, 1-octene, 1-decene, 1-dodecene, or any combination thereof.

Aspect 31. A process comprising:
(i) conducting a hydroboration-oxidation reaction of a first normal alpha olefin having the structure $CH_3(CH_2)_n HC=CH_2$ to form a linear primary alcohol having the structure $CH_3(CH_2)_{n+1}CH_2OH$; and
(ii) contacting the linear primary alcohol with the catalyst composition defined in any one of aspects 1-19 to form a second normal alpha olefin having the structure $CH_3(CH_2)_{n-1}HC=CH_2$;
wherein n is an integer from 1 to 33.

Aspect 32. A process comprising:
(i) conducting a dihydroxylation reaction of a first normal alpha olefin having the structure $CH_3(CH_2)_n HC=CH_2$ to form a terminal vicinal diol having the structure $CH_3(CH_2)_n CH(OH)CH_2OH$; and
(ii) contacting the terminal vicinal diol with the catalyst composition defined in any one of aspects 1-19 to form a second normal alpha olefin having the structure $CH_3(CH_2)_{n-2}HC=CH_2$;
wherein n is an integer from 2 to 33.

Aspect 33. The process defined in aspect 31 or 32, wherein step (ii) is performed in a solvent (e.g., toluene, THF, dioxane).

Aspect 34. The process defined in any one of aspects 31-33, wherein step (ii) is performed at a temperature from about 0° C. to about 150° C. (or any other minimum temperature, maximum temperature, or temperature range described herein).

Aspect 35. The process defined in any one of aspects 31-34, wherein a molar ratio of the acceptor to the primary alcohol (or vicinal diol) is in a range from about 0.2:1 to about 1000:1, or from about 0.5:1 to about 5:1 (or have any other minimum value, maximum value, or range described herein).

Aspect 36. The process defined in any one of aspects 31-35, wherein a molar ratio of the primary alcohol (or vicinal diol) to the transition metal of the transition metal compound or the phosphine transition metal compound complex is in a range from about 2:1 to about 1000:1, or from about 10:1 to about 250:1 (or have any other minimum value, maximum value, or range described herein).

Aspect 37. The process defined in any one of aspects 31-36, wherein a molar yield of the normal alpha olefin is at least about 20%, at least about 50%, at least about 75%, or at least about 90%, based on the primary alcohol (or vicinal diol) (or have any other value, or range described herein).

Aspect 38. The process defined in any one of aspects 31-37, wherein n is an integer from 2 to 10.

Aspect 39. The process defined in any one of aspects 31-37, wherein n is an integer from 3 to 7.

Aspect 40. The process defined in any one of aspects 31-37, wherein the second normal alpha olefin comprises propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof.

Aspect 41. The process defined in any one of aspects 31-37, wherein the second normal alpha olefin comprises 1-butene, 1-hexene, 1-octene, 1-decene, 1-dodecene, or any combination thereof.

Aspect 42. A process comprising:
(i) contacting a first normal alpha olefin having the structure $CH_3(CH_2)_n HC=CH_2$ and a metathesis catalyst system to form a linear internal olefin having the structure $CH_3(CH_2)_n HC=CH(CH_2)_n CH_3$;
(ii) contacting the linear internal olefin with a hydroformylation catalyst system, carbon monoxide, and hydrogen to form a linear aldehyde having the formula $CH_3(CH_2)_{2n+3}C(=O)H$; and
(iii) contacting the linear aldehyde with the catalyst composition defined in any one of aspects 1-19 to form a second normal alpha olefin having the structure $CH_3(CH_2)_{2n+1}HC=CH_2$;
wherein n is an integer from 0 to 15.

Aspect 43. A process comprising:
(a) contacting a linear internal olefin having the structure $CH_3(CH_2)_p HC=CH(CH_2)_q CH_3$ with a hydroformylation catalyst system, carbon monoxide, and hydrogen to form a linear aldehyde having the formula $CH_3(CH_2)_{p+q+3}C(=O)H$; and
(b) contacting the linear aldehyde with the catalyst composition defined in any one of aspects 1-19 to form a normal alpha olefin having the structure $CH_3(CH_2)_{p+q+1}HC=CH_2$;
wherein p and q independently are an integer from 0 to 15.

Aspect 44. The process defined in aspect 42 or 43, wherein step (iii) and step (b) are performed in a solvent (e.g., toluene, THF, dioxane).

Aspect 45. The process defined in any one of aspects 42-44, wherein step (iii) and step (b) are performed at a temperature from about 0° C. to about 150° C. (or any other minimum temperature, maximum temperature, or temperature range described herein).

Aspect 46. The process defined in any one of aspects 42-45, wherein a molar ratio of the acceptor to the linear aldehyde is in a range from about 0.2:1 to about 1000:1, or from about 0.5:1 to about 5:1 (or have any other minimum value, maximum value, or range described herein).

Aspect 47. The process defined in any one of aspects 42-46, wherein a molar ratio of the linear aldehyde to the transition metal of the transition metal compound or the phosphine transition metal compound complex is in a range from about 2:1 to about 1000:1, or from about 10:1 to about 250:1 (or have any other minimum value, maximum value, or range described herein).

Aspect 48. The process defined in any one of aspects 42-47, wherein a molar yield of the normal alpha olefin is at least about 20%, at least about 50%, at least about 75%, or at least about 90%, based on the linear aldehyde (or have any other value, or range described herein).

Aspect 49. The process defined in any one of aspects 42-48, wherein n, p, and q independently are an integer from 0 to 10.

Aspect 50. The process defined in any one of aspects 42-48, wherein n, p, and q independently are an integer from 1 to 7.

Aspect 51. The process defined in any one of aspects 42-48, wherein the normal (or second normal) alpha olefin comprises ethylene, propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof.

Aspect 52. The process defined in any one of aspects 42-48, wherein the normal (or second normal) alpha olefin comprises 1-butene, 1-hexene, 1-octene, 1-decene, 1-dodecene, or any combination thereof.

What is claimed is:

1. A process comprising:
   (i) conducting a dihydroxylation reaction of a first normal alpha olefin having the structure $CH_3(CH_2)_nHC=CH_2$ to form a terminal vicinal diol having the structure $CH_3(CH_2)_nCH(OH)CH_2OH$; and
   (ii) contacting the terminal vicinal diol with a catalyst composition to form a second normal alpha olefin having the structure $CH_3(CH_2)_{n-2}HC=CH_2$;
   wherein n is an integer from 2 to 33; and
   wherein the catalyst composition comprises:
   (I) a transition metal compound, a phosphine, and a heteroatomic acid or heteroatomic acid derivative; or
   (II) a phosphine transition metal compound complex and a heteroatomic acid or heteroatomic acid derivative.

2. The process of claim 1, wherein:
   the second normal alpha olefin comprises 1-hexene, 1-octene, 1-decene, 1-dodecene, 1-tetradecene, 1-hexadecene, 1-octadecene, or any combination thereof;
   the transition metal compound or the transition metal compound of the phosphine transition metal compound complex comprises an olefin rhodium alkoxide complex; and
   the heteroatomic acid or heteroatomic acid derivative comprises a carboxylic acid, an alcohol, a mineral acid, an ammonium salt, an amine, a thiol, or any combination thereof.

3. The process of claim 2, wherein:
   a molar ratio of the vicinal diol to the transition metal of the transition metal compound or the phosphine transition metal compound complex is in a range from about 2:1 to about 1000:1; and
   the heteroatomic acid or heteroatomic acid derivative comprises benzoic acid or a substituted benzoic acid, or a salt or ester of benzoic acid or a substituted benzoic acid.

4. The process of claim 1, wherein the catalyst composition further comprises an acceptor.

5. The process of claim 3, wherein the acceptor comprises an enone, an enamine, an enol, an enamide, or any combinations thereof.

6. The process of claim 3, wherein:
   the second normal alpha olefin comprises 1-hexene, 1-octene, 1-decene, 1-dodecene, 1-tetradecene, 1-hexadecene, 1-octadecene, or any combination thereof; and
   a molar ratio of the acceptor to the vicinal diol is in a range from about 0.2:1 to about 1000:1.

7. The process of claim 6, wherein a molar yield of the second normal alpha olefin is at least about 50%, based on the vicinal diol.

8. The process of claim 6, wherein:
   the transition metal compound or the transition metal compound of the phosphine transition metal compound complex comprises an olefin rhodium alkoxide complex; and
   the heteroatomic acid or heteroatomic acid derivative comprises a carboxylic acid, an alcohol, a mineral acid, an ammonium salt, an amine, a thiol, or any combination thereof.

9. The process of claim 8, wherein:
   the heteroatomic acid or heteroatomic acid derivative comprises benzoic acid or a substituted benzoic acid, or a salt or ester of benzoic acid or a substituted benzoic acid.

10. A process comprising:
    (i) contacting a first normal alpha olefin having the structure $CH_3(CH_2)_nHC=CH_2$ and a metathesis catalyst system to form a linear internal olefin having the structure $CH_3(CH_2)_nHC=CH(CH_2)_nCH_3$;
    (ii) contacting the linear internal olefin with a hydroformylation catalyst system, carbon monoxide, and hydrogen to form a linear aldehyde having the formula $CH_3(CH_2)_{2n+3}C(=O)H$; and
    (iii) contacting the linear aldehyde with a catalyst composition to form a second normal alpha olefin having the structure $CH_3(CH_2)_{2n+1}HC=CH_2$;
    wherein n is an integer from 0 to 15; and
    wherein the catalyst composition comprises:
    (I) a transition metal compound, a phosphine, a heteroatomic acid or heteroatomic acid derivative, and an acceptor; or
    (II) a phosphine transition metal compound complex, a heteroatomic acid or heteroatomic acid derivative, and an acceptor.

11. The process of claim 10, wherein:
    the second normal alpha olefin comprises 1-hexene, 1-octene, 1-decene, 1-dodecene, 1-tetradecene, 1-hexadecene, 1-octadecene, or any combination thereof; and
    a molar ratio of the acceptor to the linear aldehyde is in a range from about 0.2:1 to about 1000:1.

12. The process of claim 11, wherein the acceptor comprises an enone, an enamine, an enol, an enamide, or any combinations thereof.

13. The process of claim 11, wherein:
    a molar yield of the second normal alpha olefin is at least about 50%, based on the linear aldehyde;
    the transition metal compound or the transition metal compound of the phosphine transition metal compound complex comprises an olefin rhodium alkoxide complex; and
    the heteroatomic acid or heteroatomic acid derivative comprises a carboxylic acid, an alcohol, a mineral acid, an ammonium salt, an amine, a thiol, or any combination thereof.

14. The process of claim 11, wherein:

the heteroatomic acid or heteroatomic acid derivative comprises benzoic acid or a substituted benzoic acid, or a salt or ester of benzoic acid or a substituted benzoic acid.

15. A process comprising:

(a) contacting a linear internal olefin having the structure $CH_3(CH_2)_pHC=CH(CH_2)_qCH_3$ with a hydroformylation catalyst system, carbon monoxide, and hydrogen to form a linear aldehyde having the formula $CH_3(CH_2)_{p+q+3}C(=O)H$; and (b) contacting the linear aldehyde with a catalyst composition to form a normal alpha olefin having the structure $CH_3(CH_2)_{p+q+1}HC=CH_2$;

wherein p and q independently are an integer from 0 to 15; and wherein the catalyst composition comprises:

(I) a transition metal compound, a phosphine, a heteroatomic acid or heteroatomic acid derivative, and an acceptor; or (II) a phosphine transition metal compound complex, a heteroatomic acid or heteroatomic acid derivative, and an acceptor.

16. The process of claim 15, wherein:

the second normal alpha olefin comprises 1-hexene, 1-octene, 1-decene, 1-dodecene, 1-tetradecene, 1-hexadecene, 1-octadecene, or any combination thereof; and a molar ratio of the acceptor to the linear aldehyde is in a range from about 0.2:1 to about 1000:1.

17. The process of claim 16, wherein the acceptor comprises an enone, an enamine, an enol, an enamide, or any combinations thereof.

18. The process of claim 16, wherein:

a molar yield of the second normal alpha olefin is at least about 50%, based on the linear aldehyde;

the transition metal compound or the transition metal compound of the phosphine transition metal compound complex comprises an olefin rhodium alkoxide complex; and the heteroatomic acid or heteroatomic acid derivative comprises a carboxylic acid, an alcohol, a mineral acid, an ammonium salt, an amine, a thiol, or any combination thereof.

19. The process of claim 16, wherein:

the heteroatomic acid or heteroatomic acid derivative comprises benzoic acid or a substituted benzoic acid, or a salt or ester of benzoic acid or a substituted benzoic acid.

* * * * *